(12) United States Patent
DeJonge et al.

(10) Patent No.: US 10,376,499 B2
(45) Date of Patent: Aug. 13, 2019

(54) COMBINATION THERAPY FOR TREATMENT OF RESISTANT BACTERIAL INFECTIONS

(71) Applicant: Entasis Therapeutics Limited, Altrincham (GB)

(72) Inventors: Boudewijn Lodewijk Maria DeJonge, Waltham, MA (US); Thomas Francois Durand-Reville, Belmont, MA (US); Jeroen Cunera Verheijen, Westborough, MA (US); Ruben Tommasi, Stow, MA (US); John Mueller, Waltham, MA (US)

(73) Assignee: Entasis Therapeutics Limited, Altrincham (GB)

( * ) Notice: Subject to any disclaimer, the term of this patent is extended or adjusted under 35 U.S.C. 154(b) by 0 days.

(21) Appl. No.: 15/947,959

(22) Filed: Apr. 9, 2018

(65) Prior Publication Data
US 2018/0289681 A1 Oct. 11, 2018

Related U.S. Application Data

(62) Division of application No. 15/527,091, filed as application No. PCT/US2015/061076 on Nov. 17, 2015, now Pat. No. 9,968,593.
(Continued)

(51) Int. Cl.
*A61K 31/439* (2006.01)
*C07D 471/08* (2006.01)
(Continued)

(52) U.S. Cl.
CPC .......... *A61K 31/439* (2013.01); *A61K 31/197* (2013.01); *A61K 31/407* (2013.01); *A61K 31/43* (2013.01); *C07D 471/08* (2013.01)

(58) Field of Classification Search
None
See application file for complete search history.

(56) References Cited

U.S. PATENT DOCUMENTS

| 7,112,592 B2 | 9/2006 | Lampilas et al. |
| 7,612,087 B2 | 11/2009 | Aszodi et al. |

(Continued)

FOREIGN PATENT DOCUMENTS

| EP | 2135959 A1 | 12/2009 |
| WO | 95/18129 A1 | 7/1995 |

(Continued)

OTHER PUBLICATIONS

Akova, Eur. Society of Clinical Microbiology and Infectious Diseases, vol. 14, Jan. 1, 2008 (Jan. 1, 2008), pp. 185-188 (Year: 2008).*

(Continued)

*Primary Examiner* — Karl J Puttlitz
(74) *Attorney, Agent, or Firm* — McCarter & English, LLP; Steven G. Davis; Michael J. DeGrazia

(57) ABSTRACT

The present invention is directed to combinations of a β-lactamase inhibitor with sulbactam and, optionally, imipenem/cilastatin. The combinations are useful for the treatment of bacterial infections, including infections caused by drug resistant organisms, including multi-drug resistant pathogens. More particularly, the invention relates to a combination of β-lactamase inhibitor compound 1: or a pharmaceutically acceptable salt thereof, with sulbactam, or a pharmaceutically acceptable salt thereof, and, optionally, imipenem/cilastatin, or a pharmaceutically acceptable salt thereof.

(Continued)

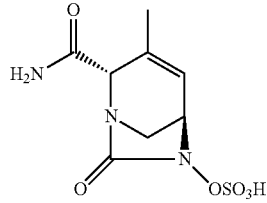

(1)

9 Claims, 9 Drawing Sheets

Related U.S. Application Data

(60) Provisional application No. 62/080,667, filed on Nov. 17, 2014.

(51) Int. Cl.
*A61K 31/197* (2006.01)
*A61K 31/407* (2006.01)
*A61K 31/43* (2006.01)

(56) References Cited

U.S. PATENT DOCUMENTS

| | | | |
|---|---|---|---|
| 9,309,245 | B2 | 4/2016 | McGuire et al. |
| 2004/0157826 | A1 | 8/2004 | Lampilas et al. |
| 2006/0046995 | A1 | 3/2006 | Lampilas et al. |
| 2010/0087648 | A1 | 4/2010 | Lampilas et al. |
| 2010/0092443 | A1* | 4/2010 | Levasseur ............ C07D 471/18 424/93.47 |
| 2010/0093784 | A1 | 4/2010 | Ledoussal et al. |
| 2010/0137355 | A1 | 6/2010 | Lampilas et al. |
| 2013/0225554 | A1 | 8/2013 | Maiti et al. |
| 2013/0289012 | A1 | 10/2013 | Gu et al. |
| 2013/0296555 | A1 | 11/2013 | Gu et al. |
| 2014/0094447 | A1 | 4/2014 | Bhagwat et al. |

FOREIGN PATENT DOCUMENTS

| | | |
|---|---|---|
| WO | 2002/010172 A1 | 2/2002 |
| WO | 2009/091856 A2 | 7/2009 |
| WO | 2009/133442 A1 | 11/2009 |
| WO | 2011/042560 A1 | 4/2011 |
| WO | 2013/014497 A1 | 1/2013 |
| WO | 2013/30733 A1 | 3/2013 |
| WO | 2013/30735 A1 | 3/2013 |
| WO | 2013/38330 A1 | 3/2013 |
| WO | 2013/149121 A1 | 10/2013 |
| WO | 2013/149136 A1 | 10/2013 |
| WO | 2013/150296 * | 10/2013 |
| WO | 2013/150296 A1 | 10/2013 |
| WO | 2013/180197 A1 | 12/2013 |
| WO | 2014/33560 A1 | 3/2014 |
| WO | 2014/033561 A1 | 3/2014 |
| WO | 2014/122468 A1 | 8/2014 |
| WO | 2014/141132 A1 | 9/2014 |
| WO | 2016/081452 A1 | 5/2016 |

OTHER PUBLICATIONS

Tetsuo Sawai et al., Diagnostic Microbiology and Infectious Diseases., vol. 12, No. 4, Jul. 1, 1989 (Jul. 1, 1989), pp. 121-129 (Year: 1989).*
Akova, Sulbactam-containing beta-lactamase inhibitor combinations. Clin Microbiol Infect. 2008;14(Suppl. 1):185-188.
Sawai et al., Mechanism of beta-lactamase inhibition: differences between sulbactam and other inhibitors. Diagn Microbiol Infect Dis. Jul.-Aug. 1989;12(4 Suppl):121S-129S.
Aszodi et al. "Design and synthesis of bridged gamma-lactams as analogues of beta-lactam antibiotics," Bioorganic & Medicinal Chemistry Letters. 14(10):2489-92 (2004).
Bonnefoy, Alain et al., "In vitro activity of AVE1330A, an innovative broad-spectrum non-beta-lactam beta-lactamase inhibitor," J Antimicrobial Chemotherapy 54(2): 410-417 (2004).
International Preliminary Report for PCT/GB2013/050869 dated Oct. 7, 2014.
International Search Report for PCT/GB2013/050869; dated May 15, 2013.
Shlaes, David "New Beta-lactam-beta-lactamase inhibitor combinations in clinical development," Annals of the New York Academy of Sciences 1277:105-114 (2013).

* cited by examiner

COMBINATION THERAPY FOR TREATMENT OF RESISTANT BACTERIAL INFECTIONS

RELATED APPLICATIONS

This application is a divisional of U.S. patent application Ser. No. 15/527,091, filed May 16, 2017, which is a 35 U.S.C. § 371 national stage filing of International Application No. PCT/US2015/061076, filed on Nov. 17, 2015, which claims the benefit of the earlier filed U.S. Provisional Application No. 62/080,667 filed on Nov. 17, 2014. The contents of each of the foregoing applications are incorporated herein by reference in their entirety.

FIELD OF THE INVENTION

The present invention relates to a novel combination of the β-lactamase inhibitor (2S,5R)-2-carbamoyl-3-methyl-7-oxo-1,6-diazabicyclo[3.2.1]oct-3-en-6-yl hydrogen sulfate (compound 1) and sulbactam, pharmaceutical compositions and methods of use. The present invention also relates to a novel combination of the β-lactamase inhibitor (2S,5R)-2-carbamoyl-3-methyl-7-oxo-1,6-diazabicyclo[3.2.1]oct-3-en-6-yl hydrogen sulfate (compound 1), sulbactam, and imipenem/cilastatin, pharmaceutical compositions and methods of use. In addition, the present invention relates to therapeutic methods for the treatment of resistant bacterial infections, including resistant and multi-drug resistant infections.

BACKGROUND OF THE INVENTION

The international microbiological and infectious disease community continues to express serious concern that the continuing evolution of antibacterial resistance could result in bacterial strains against which currently available antibacterial agents will be ineffective. The outcome of such an occurrence could have considerable morbidity and mortality.

The effectiveness of currently available therapies is limited by highly resistant infectious strains such as methicillin-resistant *Staphylococcus aureus* (MRSA) and multi-drug resistant (MDR) strains of *Pseudomonas aeruginosa, Acinetobacter baumannii, Escherichia coli, Klebsiella pneumonia*, and other Enterobacteriaceae. Such resistant bacteria are major causes of patient morbidity and mortality. Helfand, β-lactams Against Emerging 'Superbugs': Progress and Pitfalls, Expert Rev. Clin. Pharmacol. 1(4):559-571 (2008).

*Acinetobacter baumannii* has emerged globally as a cause of many serious infections such as urinary tract infections, wound and surgical site infection, bacteremia, meningitis, and nosocomial infections, including ventilator-associated pneumonia (VAP). Lee, et al., *Impact of Appropriate Antimicorbial Therapy on Mortality Associated with Acinetobacter baumannii Bacteremia*, Clinical Infectious Diseases, 55(2):209-215 (2012); Yang, et al., *Nosocomial meningitis Caused by Acinetobacter baumannii: Risk Factors and Their Impact on Patient Outcomes and Treatments*, Future Microbiology, 7(6):787-793 (2012). VAP is the most frequent *A. baumannii* infection in intensive care unit (ICU) patients, with a mortality rate of 25-75%. Chaari, et al., *Acinetobacter baumannii Ventilator-Associated Pneumonia: Epidemiology, Clinical Characteristics, and Prognosis Factors*, Int. J. Infectious Diseases, 17(12):e1225-e1228 (2013). About 63% of *A. baumannii* isolates are considered multi-drug resistant (MDR), which severely limits the treatment options, and which drives the high mortality rate. Karageorgopoulos, et al., *Current Control and Treatment of Multi-Drug Resistant Acinetobacter Infections*, Lancet, 8(12):751-762 (2008).

A major driver to the MDR resistance seen in the clinic is the increasing prevalence of extended-spectrum beta-lactamases (ESBLs). β-lactamases are enzymes that are secreted by some bacteria and can open the β-lactam ring of a β-lactam antibiotic and thereby deactivate it. There are currently four classes of β-lactamases, denoted Class A, Class B, Class C and Class D, in the Ambler classification. Class A, Class C and Class D β-lactamases are serine β-lactamase inhibitors, while Class B β-lactamases are metallo-β-lactamases (MBLs). Bush & Jacoby, *Updated Functional Classification of β-Lactamases*, Antimicrobial Agents and Chemotherapy, 54(3):969-976 (March 2010); Ambler, R. P., *The Structure of Beta-Lactamases*, Philos. Trans. R. Soc. London B; 289:321-331 (May 1980).

To help improve the effectiveness of β-lactam antibiotics, some β-lactamase inhibitors have been developed. However, typical β-lactamase inhibitors in many instances are insufficient to counter the constantly increasing diversity of β-lactamases. Most currently available β-lactamase inhibitors have activity primarily against certain Class A enzymes, which severely limits their utility. Additionally, new β-lactamase inhibitors, such as avibactam (approved in the US in 2015) and relebactam (MK-7655, still in clinical trials) work primarily on Class A and C enzymes, with minimal effectiveness against Class D β-lactamases. Bebrone, et al., *Current Challenges in Antimicrobial Chemotherapy: Focus on β-Lactamase Inhibition*, Drugs, 70(6):651-679 (2010).

Sulbactam is the Class A β-lactamase inhibitor (2S,5R)-3,3-dimethyl-7-oxo-4-thia-1-azabicyclo[3.2.0]heptane-2-carboxylic acid 4,4-dioxide. In addition to being a β-lactamase inhibitor, it also has intrinsic activity against a few pathogens, including *Acinetobacter baumannii*. Currently, sulbactam is commercially available in the United States in combination with ampicillin, which is marketed as Unasyn® and is approved in the US for treatment of skin, gynecological and intra-abdominal infections; it is also sold in the US as an oral agent Sultamicillin®. Adnan, et al., *Ampicillin/Sulbactam: Its Potential Use in Treating Infections in Critically Ill Patients*, Int. J. Antimicrobial Agents, 42(5):384-389 (2013). Clinically, Unasyn® has been used to treat VAP, bacteremia and other nosocomial infections caused by *A. baumannii*, even though ampicillin has no activity against the pathogen. However, significant resistance is emerging in the clinic. Jones, et al., *Resistance Surveillance Program Report for Selected European Nations*, Diagnostic Microbiology & Infectious Disease, 78(4): 429-436 (2011). Sulbactam is also commercially available in certain regions of the world in combination with cefoperasone and is sold as Cefina-SB®, Sulperazone® or Bacperazone®, depending on the geographic region.

While sulbactam is itself a β-lactamase inhibitor, it does not possess activity against many clinically relevant β-lactamases such as TEM-1 and *Klebsiella pneumonia* carbapenemases (KPCs), in addition to having no activity against most Class C and Class D β-lactamases. See Table 1. This upsurge in resistance means that sulbactam will have less and less clinical efficacy for patients with *Acinetobacter* spp. infections.

Imipenem/cilastatin is a broad-spectrum antibiotic with activity against many Gram-negative and Gram-positive organisms, including, but not limited to, *Acinetobacter* spp., *Citrobacter* spp., *Escheriachia coli, Haemophilus influenzae, Haemophilus parainfluenzae, Klebsiella* spp., *Morganella morganii, Pseudomonas aeruginosa, Enterobacter* spp., Staphylococcus aureus, Streptococcus agalactiae, Streptococcus pneumonia, Streptococcus pyogenes, Enterococcus faecalis, Clostridium spp., and Bifidobacterium spp., among others. However, resistance to imipenem is emerging, especially in Pseudomonas aeruginosa infections. See, e.g., Lautenbach, et al., "Imipenem Resistance in Pseudomonas aeruginosa: Emergence, Epidemiology and Impact on Clinical and Economic Outcomes", Infect. Control Hospital Epidemiol., (2010) 31(1):47-53. Resistant strains of Pseudomonas aeruginosa to carbapenems such as imipenem have been increasing, and are associated with longer hospital stays, increased healthcare spend and higher mortality. See Liu et al., "Influence of Carbapenem Resistance on Mortality of Patients with Pseudomonas aeruginosa Infection: a Meta-Analysis", Nature: Scientific Reports (2015), 5:11715.

There is a clear and urgent need for a treatment for infections caused by resistant, and MDR, bacterial infections, which already have a high mortality rate, and which will only prove more deadly as resistance to current treatments grows.

SUMMARY OF THE INVENTION

The present invention is directed to a combination of a β-lactamase inhibitor, compound 1, or a pharmaceutically acceptable salt thereof, with sulbactam, or a pharmaceutically acceptable salt thereof. The combination is useful for the treatment of Acinetobacter spp., Pseudomonas aeruginosa, Enterobacteriaceae and/or Burkholderia spp., including infections caused by drug resistant strains, including MDR A. baumannii. More particularly, the invention relates to a combination of the β-lactamase inhibitor compound 1,

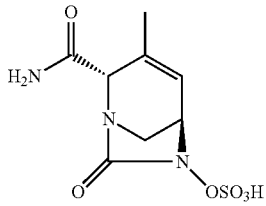

or a pharmaceutically acceptable salt thereof, with sulbactam:

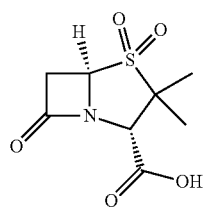

or a pharmaceutically acceptable salt thereof.

The present invention is also directed to a combination of a β-lactamase inhibitor, compound 1, or a pharmaceutically acceptable salt thereof, with sulbactam, or a pharmaceutically acceptable salt thereof, imipenem, or a salt thereof, and cilastatin or a salt thereof. The combination is useful for the treatment of bacterial infections caused by pathogens such as Acinetobacter spp., Pseudomonas aeruginosa, Enterobacteriaceae and/or Burkholderia spp., including infections caused by drug resistant strains. More particularly, the invention relates to a combination of the β-lactamase inhibitor compound 1:

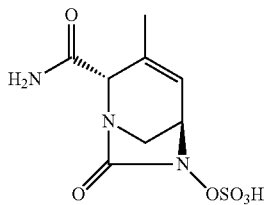

or a pharmaceutically acceptable salt thereof; sulbactam:

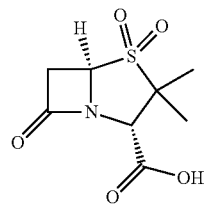

or a pharmaceutically acceptable salt thereof; imipenem:

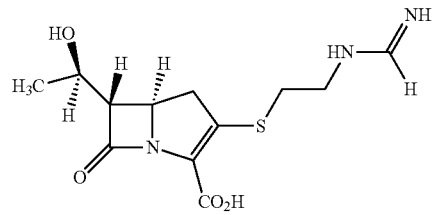 [SMILES: C[C@@H](O)[C@H]1C(=O)N2C(C(=O)O)=C(SCCNC=N)C[C@H]12]

or a pharmaceutically acceptable salt thereof; and cilastatin:

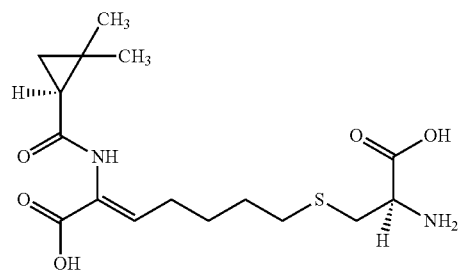 [SMILES: CC1(C)C[C@@H]1C(=O)N/C(=C\CCCCSC[C@H](N)C(=O)O)C(=O)O]

or a pharmaceutically acceptable salt thereof.

DETAILED DESCRIPTION OF THE INVENTION

Figure 1:
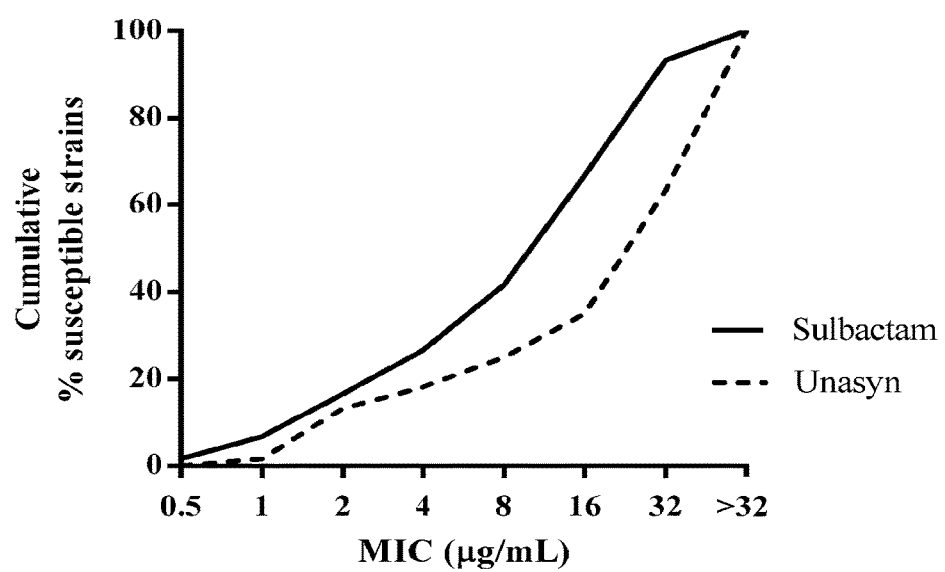
FIG. 1 shows a comparison of sulbactam versus Unasyn®. Sulbactam is more active than Unasyn® (a combination of sulbactam and ampicillin in a 1:2 ratio) against a panel of recent A. baumannii clinical isolates (n=60; listed in Table 1).

The present invention provides a combination comprising, consisting essentially of, or consisting of, the β-lactamase inhibitor compound 1:

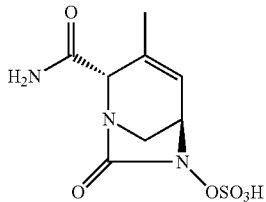

or a pharmaceutically acceptable salt thereof, with sulbactam, or a pharmaceutically acceptable salt thereof (hereinafter referred to as "the double combination"). The double combination is useful for the treatment of bacterial infections caused by pathogens including, but not limited to, *Acinetobacter* spp., *Pseudomonas aeruginosa*, Enterobacteriaceae and/or *Burkholderia* spp., including infections caused by drug resistant strains.

The present invention is also directed to a combination of a β-lactamase inhibitor, compound 1, or a pharmaceutically acceptable salt thereof, with sulbactam, or a pharmaceutically acceptable salt thereof, imipenem, or a pharmaceutically acceptable salt thereof, and cilastatin or a pharmaceutically acceptable salt thereof (hereinafter referred to as "the quad combination"). The quad combination is useful for the treatment of bacterial infections caused by pathogens including, but not limited to, *Acinetobacter* spp., *Pseudomonas aeruginosa*, Enterobacteriaceae and/or *Burkholderia* spp., including infections caused by drug resistant strains. More particularly, the invention relates to a combination comprising, consisting essentially of, or consisting of the β-lactamase inhibitor compound 1:

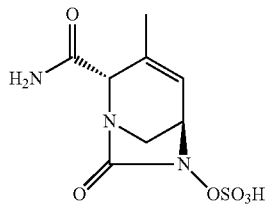

or a pharmaceutically acceptable salt thereof; sulbactam, or a pharmaceutically acceptable salt thereof; imipenem, or a pharmaceutically acceptable salt thereof; and cilastatin, or a pharmaceutically acceptable salt thereof.

In one embodiment, the double combination comprises an effective amount of compound 1, or a pharmaceutically acceptable salt thereof, and an effective amount of sulbactam, or a pharmaceutically acceptable salt thereof. In a second embodiment, the double combination consists essentially of an effective amount of compound 1, or a pharmaceutically acceptable salt thereof, and an effective amount of sulbactam, or a pharmaceutically acceptable salt thereof. In a third embodiment, the double combination consists essentially of an effective amount of compound 1, or a pharmaceutically acceptable salt thereof, and an effective amount of sulbactam, or a pharmaceutically acceptable salt thereof, and one or more pharmaceutically acceptable carriers, diluents and/or excipients, and optionally, ampicillin or cefoperazone, or a pharmaceutically acceptable salt thereof. In a fourth embodiment, the double combination consists of an effective amount of compound 1, or a pharmaceutically acceptable salt thereof, and an effective amount of sulbactam, or a pharmaceutically acceptable salt thereof. In a fifth embodiment, the double combination consists of an effective amount of compound 1, or a pharmaceutically acceptable salt thereof, and an effective amount of sulbactam, or a pharmaceutically acceptable salt thereof, and one or more pharmaceutically acceptable carriers, diluents and/or excipients, and optionally, ampicillin or cefoperazone, or a pharmaceutically acceptable salt thereof. In any of the above five embodiments, the effective amount of sulbactam, or a pharmaceutically acceptable salt thereof, component of the combination may be provided in the form of a Unasyn®, Cefina-SB®, Sulperazone®, Sultamicillin® or Bacperazone® product, wherein the combination further contains ampicillin or cefoperazone, or a pharmaceutically acceptable salt thereof.

In any embodiment of the double combination, compound 1, or a pharmaceutically acceptable salt thereof, and the sulbactam, or a pharmaceutically acceptable salt thereof, may be administered separately or concurrently. Separate administration of compound 1, or a pharmaceutically acceptable salt thereof, and sulbactam, or a pharmaceutically acceptable salt thereof, includes sequential administration of compound 1, or a pharmaceutically acceptable salt thereof, and sulbactam, or a pharmaceutically acceptable salt thereof, in any order of administration. Concurrent administration of compound 1, or a pharmaceutically acceptable salt thereof, and sulbactam, or a pharmaceutically acceptable salt thereof, includes co-administering the compound 1 and sulbactam as part of a single pharmaceutical composition, or as two pharmaceutical compostions administered simultaneously for at least part of total period of administration.

One embodiment of the quad combination comprises an effective amount of compound 1, or a pharmaceutically acceptable salt thereof, an effective amount of sulbactam, or a pharmaceutically acceptable salt thereof, an effective amount of imipenem, or a pharmaceutically acceptable salt thereof, and an effective amount of cilastatin, or a pharmaceutically acceptable salt thereof. In a second embodiment, the quad combination consists essentially of an effective amount of compound 1, or a pharmaceutically acceptable salt thereof, an effective amount of sulbactam, or a pharmaceutically acceptable salt thereof, an effective amount of imipenem, or a pharmaceutically acceptable salt thereof, and an effective amount of cilastatin, or a pharmaceutically acceptable salt thereof. In a third embodiment, the quad combination consists essentially of an effective amount of compound 1, or a pharmaceutically acceptable salt thereof, an effective amount of sulbactam, or a pharmaceutically acceptable salt thereof, an effective amount of imipenem, or a pharmaceutically acceptable salt thereof, and an effective amount of cilastatin, or a pharmaceutically acceptable salt thereof, and one or more pharmaceutically acceptable carriers, diluents and/or excipients, and, optionally, ampicillin or cefoperazone, or a pharmaceutically acceptable salt thereof. In a fourth embodiment, the quad combination consists of an effective amount of compound 1, or a pharmaceutically acceptable salt thereof, an effective amount of sulbactam, or a pharmaceutically acceptable salt thereof, an effective amount of imipenem, or a pharmaceutically acceptable salt thereof, and an effective amount of cilastatin, or a pharmaceutically acceptable salt thereof. In a fifth embodiment, the quad combination consists of an effective amount of compound 1, or a pharmaceutically acceptable salt thereof, an effective amount of sulbactam, or a pharmaceutically acceptable salt thereof, an effective amount of imipenem, or a pharmaceutically acceptable salt thereof, and an effective amount of cilastatin, or a pharmaceutically acceptable salt thereof, and one or more pharmaceutically acceptable carriers, diluents and/or excipients, and, optionally, ampicillin or cefoperazone, or a pharmaceutically acceptable salt thereof. In any of the above five embodiments, the effective amount of sulbactam, or a pharmaceutically acceptable salt thereof, component of the combination may be provided in the form of a Unasyn®, Cefina-SB®, Sulperazone®, Sultamicillin® or Bacperazone® product, wherein the combination further contains ampicillin or cefoperazone, or a pharmaceutically acceptable salt thereof. Additionally, for any of the embodiments disclosed in the present paragraph, the effective amount of imipenem and the effective amount of cilastatin, or pharmaceutically acceptable salts thereof, may be present in the form of the combination product Primaxin®.

In any embodiment of the quad combination, compound 1, or a pharmaceutically acceptable salt thereof, sulbactam, or a pharmaceutically acceptable salt thereof, imipenem, or a pharmaceutically acceptable salt thereof, and cilastatin or a pharmaceutically acceptable salt thereof, may be administered separately or concurrently. Separate administration of compound 1, or a pharmaceutically acceptable salt thereof, sulbactam, or a pharmaceutically acceptable salt thereof, imipenem, or a pharmaceutically acceptable salt thereof, and cilastatin or a pharmaceutically acceptable salt thereof, includes sequential administration of one or more component, in any order of administration. Sequential administration includes administering three or less of the four components concurrently, followed by administration of the remaining components of the combination. Concurrent administration of compound 1, or a pharmaceutically acceptable salt thereof, sulbactam, or a pharmaceutically acceptable salt thereof, imipenem, or a pharmaceutically acceptable salt thereof, and cilastatin or a pharmaceutically acceptable salt thereof, includes co-administering the compound 1, sulbactam, imipenem and cilastatin as part of a single pharmaceutical composition, or as two or more pharmaceutical compostions which are administered simultaneously for at least part of total period of administration. For example, compound 1 and sulbactam may be formulated in one pharmaceutical formulation, and imipenem and cilastatin may be formulated together in a separate pharmaceutical formulation, and the two formulations may be administered sequentially, in either order, with the period of administration optionally overlapping for some, or all, of the time. Typically, imipenem and cilastatin, and pharmaceutically acceptable salts thereof, are formulated in a single pharmaceutical composition and are co-administered.

Pharmaceutically Acceptable—

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Effective Amount—

As used herein, the phrase "effective amount" with respect to "compound 1", "sulbactam" and/or "imipenem" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The exact dose will depend on the purpose of the treatment, and will be ascertainable by one skilled in the art using known techniques (see, e.g., Lloyd (1999) The Art, Science and Technology of Pharmaceutical Compounding). An "effective amount of cilastatin" is the amount needed to sufficiently prevent degradation of the imipenem component of the combination by renal dehydropeptidase enzymes to allow for a clinically effective amount of imipenem to be administered to the patient. Typically, an "effective amount of cilastatin" is approximately the same weight of cilastatin as the imipenem used.

Sulbactam—

As used herein, "sulbactam" refers to (2S,5R)-3,3-dimethyl-7-oxo-4-thia-1-azabicyclo[3.2.0]heptane-2-carboxylic acid 4,4-dioxide, which is the chemical entity represented by the structure:

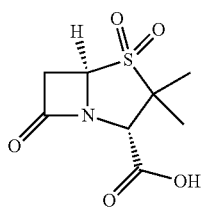

or a pharmaceutically acceptable salt thereof, in any physical form, e.g., crystalline or amorphous. The term "sulbactam" as used herein also includes the commercially relevant formulations which contain (2S,5R)-3,3-dimethyl-7-oxo-4-thia-1-azabicyclo[3.2.0]heptane-2-carboxylic acid 4,4-dioxide, sodium salt, including combination products that contain sulbactam in addition to ampicillin or cefoperazone, or salts thereof, also referred to herein as a "sulbactam+ ampicillin or cefoperazone combination product". For the avoidance of doubt, the terms "sulbactam" and "sulbactam+ ampicillin or cefoperazone combination product" include, but are not limited to, Unasyn®, Cefina-SB®, Sulperazone®, Sultamicillin® and Bacperazone®.

Imipenem— as used herein, "imipenem" refers to (5R,6S)-3-[[2-(formimidoylamino)ethyl]thio]-6-[(R)-1-hydroxyethyl]-7-oxo-1-azabicyclo[3.2.0]hept-2-ene-2-carboxylic acid, or a pharmaceutically acceptable salt and/or hydrate thereof, in any physical form, e.g., crystalline or amorphous. Typically the term "imipenem" refers to crystalline (5R,6S)-3-[[2-(formimidoylamino)ethyl]thio]-6-[(R)-1-hydroxyethyl]-7-oxo-1-azabicyclo[3.2.0]hept-2-ene-2-carboxylic acid monohydrate, but the anhydrous form is also included within the meaning of the term. The term "imipenem" also includes any and all commercially relevant formulations which contain (5R,6S)-3-[[2-(formimidoylamino)ethyl]thio]-6-[(R)-1-hydroxyethyl]-7-oxo-1-azabicyclo[3.2.0]hept-2-ene-2-carboxylic acid, or a pharmaceutically acceptable salt and/or hydrate thereof, namely combination products which contain imipenem in addition to cilastatin. Since imipenem is rapidly degraded by the renal enzyme dehydropeptidase 1 when administered alone, it is always co-administered with cilastatin, which is an inhibitor of dehydropeptidase. Thus, commercially relevant formulations of "imipenem" include products which contain at least both imipenem and cilastatin, such as Primaxin®, and generic equivalents thereof.

Cilastatin—

As used herein, "cilastatin" refers to (Z)-7-[[(R)-2-amino-2-carboxyethyl]thio]-2-[(S)-2,2-dimethylcyclopropanecarboxamido]-2-heptanoate, and pharmaceutically acceptable salts thereof, in any physical form, e.g., crystalline or amorphous. Typically, cilastatin is in the form of an amorphous sodium salt, but all salt forms and/or hydrated forms are included within the meaning of the term.

"Imipenem/cilastatin"—as used herein, refers to the combination of imipenem, or a pharmaceutically acceptable salt thereof, and cilastatin, or a pharmaceutically acceptable salt thereof. It also includes commercially relevant formulations which contain at least both imipenem and cilastatin, such as Primaxin®, and generic equivalents thereof.

Compound 1, sulbactam, imipenem, and/or cilastatin may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods), it is favorably provided substantially isolated from other stereoisomers of the same compound. In one aspect, a mixture containing a particular stereoisomer of compound 1 and/or sulbactam may contain less than 30%, particularly less than 20%, and more particularly less than 10% by weight of other stereoisomers of the same compound. In another aspect, a mixture containing a particular stereoisomer of compound 1 and/or sulbactam may contain less than 6%, particularly less than 3%, and more particularly less than 2% by weight of other stereoisomers of the compound. In another aspect, a mixture containing a particular stereoisomer of compound 1 and/or sulbactam may contain less than 1%, particularly less than 0.5%, and more particularly less than 0.3%, and still more particularly less 0.1% by weight of other stereoisomers of the compound.

It is to be understood that, insofar as compound 1, sulbactam, impenem and/or cilastatin defined above may exist in tautomeric forms, the invention includes in its definition any such tautomeric form which possesses the above-mentioned activity. Thus, the invention relates to all tautomeric forms of compound 1 and/or sulbactam whether explicitly detailed in the specification or not.

In one aspect, the terms "infection" and "bacterial infection" may refer to a gynecological infection. In another aspect the terms "infection" and "bacterial infection" may refer to a respiratory tract infection (RTI). In still another, the terms "infection" and "bacterial infection" may refer to a sexually transmitted disease. In yet another aspect, the terms "infection" and "bacterial infection" may refer to a urinary tract infection (UTI). In yet another aspect, the terms "infection" and "bacterial infection" may refer to a complicated urinary tract infection (cUTI). In a further aspect, the terms "infection" and "bacterial infection" may refer to acute exacerbation of chronic bronchitis (ACEB). In yet a further aspect, the terms "infection" and "bacterial infection" may refer to acute otitis media. In one aspect, the terms "infection" and "bacterial infection" may refer to acute sinusitis. In another aspect, the terms "infection" and "bacterial infection" may refer to an infection caused by drug resistant bacteria. In still another aspect, the terms "infection" and "bacterial infection" may refer to catheter-related sepsis. In yet another aspect, the terms "infection" and "bacterial infection" may refer to chancroid. In a further aspect, the terms "infection" and "bacterial infection" may refer to *chlamydia*. In still a further aspect, the terms "infection" and "bacterial infection" may refer to community-acquired pneumonia (CAP). In yet a further aspect, the terms "infection" and "bacterial infection" may refer to complicated skin and skin structure infection (cSSSI). In yet a further aspect, the terms "infection" and "bacterial infection" may refer to an acute bacterial skin and skin-structure infection (AB-SSSI). In one aspect, the terms "infection" and "bacterial infection" may refer to uncomplicated skin and skin structure infection (SSSI). In another aspect, the terms "infection" and "bacterial infection" may refer to endocarditis. In still another aspect, the terms "infection" and "bacterial infection" may refer to febrile neutropenia. In yet another aspect, the terms "infection" and "bacterial infection" may refer to gonococcal cervicitis. In a further aspect, the terms "infection" and "bacterial infection" may refer to gonococcal urethritis. In still a further aspect, the terms "infection" and "bacterial infection" may refer to hospital-acquired pneumonia (HAP). In still a further aspect, the terms "infection" and "bacterial infection" may refer to ventilator-associated pneumonia (VAP). In still a further aspect, the terms "infection" and "bacterial infection" may refer to infections in an immuno-compromised host, such as liver abcesses, biliary tract infections and/or bacteremia. In still a further aspect, the terms "infection" and "bacterial infection" may refer to bacteremia. In yet another aspect, the terms "infection" and "bacterial infection" may refer to osteomyelitis. In a further aspect, the terms "infection" and "bacterial infection" may refer to sepsis. In still a further aspect, the terms "infection" and "bacterial infection" may refer to syphilis. In a further aspect, the terms "infection" and "bacterial infection" may refer to an intra-abdominal infection (IAI). In a further aspect, the terms "infection" and "bacterial infection" may refer to pneumonic, septicemic and/or bubonic plague. In a further aspect, the terms "infection" and "bacterial infection" may refer to anthrax. In a further aspect, the terms "infection" and "bacterial infection" may refer to glanders. In a further aspect, the terms "infection" and "bacterial infection" may refer to melioidosis. In a further aspect, the terms "infection" and "bacterial infection" may refer to tularemia.

In one embodiment of the invention, the terms "infection" and "bacterial infection" refer to a infection caused by Gram-negative bacteria, also referred to as a "Gram-negative infection". In one aspect of this embodiment, the Gram-negative infection is an infection resistant to one or more antibiotics. In one aspect of this embodiment, the Gram-negative infection is a multi-drug resistant infection. In certain embodiments, the Gram-negative bacterium is *Acinetobacter* spp. In certain embodiments, the Gram-negative bacterium is *Acinetobacter* spp., such as *Acinetobacter baumannii*. In certain embodiments, the Gram-negative bacterium is *Burkholderia* spp. In certain embodiments, the Gram-negative bacterium is *Burkholderia pseudomallei*. In certain embodiments, the Gram-negative bacterium is *Pseudomonas aeruginosa*. In certain embodiments, the Gram-negative bacterium is Enterobacteriaceae. In any of these embodiments, the Gram-negative infection arises from a pathogen or pathogen expressing one or more β-lactamase. In any of these embodiments, the Gram-negative infection arises from a pathogen or pathogen expressing one or more Class A, Class C and/or Class D β-lactamase. In any of these embodiments, the Gram-negative infection arises from a pathogen or pathogen expressing one or more Class A β-lactamase. In any of these embodiments, the Gram-negative infection arises from a pathogen or pathogen expressing one or more Class C β-lactamase. In any of these embodiments, the Gram-negative infection arises from a pathogen or pathogen expressing one or more Class D β-lactamase.

An infection caused by "Enterobacteriaceae" refers to any of the Gram-negative bacteria in this family of bacteria which includes, but is not limited to, species such as *Salmonella* spp., *Escherichia coli*, *Yersinia pestis*, *Klebsiella* spp., *Shigella* spp., *Proteus* spp., *Enterobacter* spp., *Serratia* spp., and *Citrobacter* spp. Thus, treatment of a bacterial infection caused by "Enterobacteriaceae" includes any infection caused by any one or more bacteria which is part of this family. In one embodiment, a bactertial infection caused by "Enterobacteriaceae" includes bacterial infections which have at least one *Salmonella* spp. pathogen present. In one embodiment, a bactertial infection caused by "Enterobacteriaceae" includes bacterial infections which have at least one *Escherichia coli* pathogen present. In one embodiment, a bactertial infection caused by "Enterobacteriaceae" includes bacterial infections which have at least one *Yersinia pestis* pathogen present. In one embodiment, a bactertial infection caused by "Enterobacteriaceae" includes bacterial infections which have at least one *Klebsiella* spp. pathogen present. In one embodiment, a bactertial infection caused by "Enterobacteriaceae" includes bacterial infections which have at least one *Shigella* spp. pathogen present. In one embodiment, a bactertial infection caused by "Enterobacteriaceae" includes bacterial infections which have at least one *Proteus* spp. pathogen present. In one embodiment, a bactertial infection caused by "Enterobacteriaceae" includes bacterial infections which have at least one *Enterobacter* spp. pathogen present. In one embodiment, a bactertial infection caused by "Enterobacteriaceae" includes bacterial infections which have at least one *Serratia* spp. pathogen present. In one embodiment, a bacterial infection caused by "Enterobacteriaceae" includes bacterial infections which have at least one *Citrobacter* spp. pathogen present.

In certain embodiments, the terms "infection" and "bacterial infection" refer to a infection caused by Gram-negative bacteria, wherein the Gram-negative bacterium is Enterobacteriaceae which expresses one or more Class A, Class B, Class C and/or Class D β-lactamase. In one aspect of this embodiment, the Gram-negative bacterium is an Enterobacteriaceae which expresses at least one Class B β-lactamase.

In certain embodiments, the Gram-negative bacterium is *Acinetobacter* spp. which expresses one or more β-lactamases. In one embodiment, the Gram-negative bacterium is *Acinetobacter baumannii* which expresses one or more Class A, Class C and/or Class D β-lactamase. In one embodiment, the Gram-negative bacterium is *Acinetobacter baumannii* which expresses one or more Class A β-lactamase. In one embodiment, the Gram-negative bacterium is *Acinetobacter baumannii* which expresses one or more Class C β-lactamase. In one embodiment, the Gram-negative bacterium is *Acinetobacter baumannii* which expresses one or more Class D β-lactamase. In one embodiment, the Gram-negative bacterium is *Acinetobacter baumannii* which expresses TEM-1 or KPC-2.

All the above mentioned infections can be caused by a variety of bacteria that potentially could be treatable with an effective amount of the combination of compound 1, or a pharmaceutically acceptable salt thereof, with sulbactam, or a pharmaceutically acceptable salt thereof.

All the above mentioned infections can be caused by a variety of bacteria that potentially could be treatable with an effective amount of the combination of compound 1, or a pharmaceutically acceptable salt thereof, sulbactam, or a pharmaceutically acceptable salt thereof, imipenem, or a pharmaceutically acceptable salt thereof, and cilastatin or a pharmaceutically acceptable salt thereof.

The present disclosure provides certain methods of treating one or more of the infections listed above in a subject in need thereof, comprising, consisting essentially of, or consisting of administering to the subject an effective amount of a combination of compound 1, or a pharmaceutically acceptable salt thereof, and sulbactam, or a pharmaceutically acceptable salt thereof. These methods are particularly aimed at therapeutic treatments of animals, and more particularly, humans.

The present disclosure provides certain methods of treating one or more of the infections listed above in a subject in need thereof, comprising, consisting essentially of, or consisting of administering to the subject an effective amount of a combination of compound 1, or a pharmaceutically acceptable salt thereof, sulbactam, or a pharmaceutically acceptable salt thereof, imipenem, or a pharmaceutically acceptable salt thereof, and cilastatin or a pharmaceutically acceptable salt thereof. These methods are particularly aimed at therapeutic treatments of animals, and more particularly, humans.

In another aspect, there is provided a method for producing a bacterial peptidoglycan inhibitory effect in a warm-blooded animal such as man, said method comprising administering to said animal an effective amount of a combination of compound 1, or a pharmaceutically acceptable salt thereof, and sulbactam, or a pharmaceutically acceptable salt thereof.

In another aspect, there is provided a method for producing a bacterial peptidoglycan inhibitory effect in a warm-blooded animal such as man, said method comprising administering to said animal an effective amount of a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof.

In an additional embodiment, there is provided a method of treating Gram-negative bacterial infections in a warm-blooded animal such as man, said method comprising, consisting of, or consisting essentially of, administering to said animal an effective amount of a combination of compound 1, or a pharmaceutically acceptable salt thereof, and sulbactam, or a pharmaceutically acceptable salt thereof. In certain such embodiments, the Gram-negative infection is an infection resistant to one or more antibiotics. In certain embodiments of the foregoing, the Gram-negative bacterium *Acinetobacter* spp., such as *Acinetobacter baumannii*. In certain of the foregoing embodiments, the Gram-negative bacterium is MDR *A. baumannii*.

In a further embodiment, there is provided a method of treating Gram-negative bacterial infections in a warm-blooded animal such as man, said method comprising, consisting of, or consisting essentially of, administering to said animal an effective amount of a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof. In certain such embodiments, the Gram-negative infection is an infection resistant to one or more antibiotics. In certain embodiments of the foregoing, the Gram-negative bacterium *Acinetobacter* spp., such as *Acinetobacter baumannii*. In certain of the foregoing embodiments, the Gram-negative bacterium is MDR *A. baumannii*.

In a further aspect, there is provided a method for treating a bacterial infection in a warm-blooded animal such as man, said method comprising, consisting essentially of, or consisting of, administering to said animal an effective amount of the double combination of compound 1, or a pharmaceutically acceptable salt thereof, and sulbactam, or a pharmaceutically acceptable salt thereof. In one embodiment, the components of the combination are part of a single pharmaceutical composition and administered together. Alternatively, compound 1, or a pharmaceutically acceptable salt thereof, and the sulbactam, or a pharmaceutically acceptable salt thereof, are formulated and administered separately, either sequentially or concurrently.

In a further aspect, there is provided a method for treating a bacterial infection in a warm-blooded animal such as man, said method comprising, consisting essentially of, or consisting of, administering to said animal an effective amount of the quad combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof. In one embodiment, the components of the quad combination are part of a single pharmaceutical composition and administered together. Alternatively, compound 1, or a pharmaceutically acceptable salt thereof, the sulbactam, or a pharmaceutically acceptable salt thereof, and the imipenem, or a pharmaceutically acceptable salt thereof and the cilastatin or a pharmaceutically acceptable salt thereof, are formulated and administered in two or more separate formulations, which may then be administered sequentially or concurrently.

In still a further aspect, there is provided a method for treating urinary tract infections (including cUTI), pneumonia (including VAP and HAP), bacteremia, meningitis and/or wound and surgical site infections, in a warm-blooded animal such as man, said method comprising, consisting essentially of, or consisting of, administering to said animal an effective amount of a combination of compound 1, or a pharmaceutically acceptable salt thereof, and sulbactam, or a pharmaceutically acceptable salt thereof. In one aspect of this embodiment, the infection is caused by one or more pathogens expressing one or more β-lactamase which sulbactam alone cannot effectively inhibit.

In still a further aspect, there is provided a method for treating urinary tract infections (including cUTI), pneumonia (including VAP and HAP), bacteremia, and/or skin and skin-structure infections (SSSI) (also known as acute bacterial skin and skin structure infections (ABSSSI)), in a warm-blooded animal such as man, said method comprising, consisting essentially of, or consisting of, administering to said animal an effective amount of the quad combination of compound 1, or a pharmaceutically acceptable salt thereof, sulbactam, or a pharmaceutically acceptable salt thereof, and imipenem, or a pharmaceutically acceptable salt thereof, and cilastatin, or a pharmaceutically acceptable salt thereof. In one aspect of this embodiment, the infection is caused by one or more pathogens expressing one or more β-lactamase which sulbactam alone cannot effectively inhibit.

In one embodiment of the invention is the combination of compound 1, or a pharmaceutically acceptable salt thereof, and sulbactam, or a pharmaceutically acceptable salt thereof, for use in the treatment of one or more of the infections listed above.

In one embodiment of the invention is the use of a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of one or more of the infections listed above.

In another aspect, there is provided a combination of compound 1, or a pharmaceutically acceptable salt thereof, and sulbactam, or a pharmaceutically acceptable salt thereof, for use in the treatment of Gram-negative bacterial infections. In certain such embodiments, the Gram-negative infection is an infection resistant to one or more antibiotics. In certain embodiments, the Gram-negative infection is caused by a Gram-negative bacterium that is resistant to treatment with sulbactam in the absence of an additional β-lactamase inhibitor. In certain embodiments of the foregoing, the Gram-negative bacterium is *Acinetobacter* spp., such as *Acinetobacter baumannii*. In any of these embodiments, the Gram-negative infection from a pathogen or pathogen expressing one or more β-lactamase. In any of these embodiments, the Gram-negative infection from a pathogen or pathogen expressing one or more Class A, Class C and/or Class D β-lactamase. In any of these embodiments, the Gram-negative infection from a pathogen or pathogen expressing one or more Class A β-lactamase. In any of these embodiments, the Gram-negative infection from a pathogen or pathogen expressing one or more Class C β-lactamase. In any of these embodiments, the Gram-negative infection from a pathogen or pathogen expressing one or more Class D β-lactamase.

In another aspect, there is provided a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of Gram-negative bacterial infections. In certain such embodiments, the Gram-negative infection is an infection resistant to one or more antibiotics. In certain embodiments, the Gram-negative infection is caused by a Gram-negative bacterium that is resistant to treatment with sulbactam in the absence of an additional β-lactamase inhibitor. In certain embodiments of the foregoing, the Gram-negative bacterium is *Acinetobacter* spp., such as *Acinetobacter baumannii*. In any of these embodiments, the Gram-negative infection from a pathogen or pathogen expressing one or more β-lactamase. In any of these embodiments, the Gram-negative infection from a pathogen or pathogen expressing one or more Class A, Class C and/or Class D β-lactamase. In any of these embodiments, the Gram-negative infection from a pathogen or pathogen expressing one or more Class A β-lactamase. In any of these embodiments, the Gram-negative infection from a pathogen or pathogen expressing one or more Class C β-lactamase. In any of these embodiments, the Gram-negative infection from a pathogen or pathogen expressing one or more Class D β-lactamase.

In another aspect, there is provided the use a combination of compound 1, or a pharmaceutically acceptable salt thereof, and sulbactam, or a pharmaceutically acceptable salt thereof, in the manufacture of a medicament for the treatment of a bacterial infection in a warm-blooded animal such as man.

In another aspect, there is provided the use a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, in the manufacture of a medicament for the treatment of a bacterial infection in a warm-blooded animal such as man.

In still another aspect, there is provided the combination of compound 1, or a pharmaceutically acceptable salt thereof, and sulbactam, or a pharmaceutically acceptable salt thereof, for use in the treatment of urinary tract infections (including cUTI), pneumonia (including VAP and HAP), bacteremia, meningitis and/or wound and surgical site infections, in a warm-blooded animal such as man. In one aspect of this embodiment, the infection is caused by one or more pathogens expressing one or more β-lactamase which is not effectively inhibited by sulbactam alone.

In still another aspect, there is provided the combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of urinary tract infections (including cUTI), pneumonia (including VAP and HAP), bacteremia, and/or skin and skin-structure infections, in a warm-blooded animal such as man. In one aspect of this embodiment, the infection is caused by one or more pathogens expressing one or more β-lactamase which is not effectively inhibited by sulbactam alone.

In yet a further aspect, there is provided a combination of compound 1, or a pharmaceutically acceptable salt thereof, and sulbactam, or a pharmaceutically acceptable salt thereof, for use in producing a bacterial peptidoglycan inhibitory effect in a warm-blooded animal such as man.

In yet a further aspect, there is provided a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in producing a bacterial peptidoglycan inhibitory effect in a warm-blooded animal such as man.

In one aspect of the invention, there is provided a method of producing a peptidoglycan inhibitory effect and inhibiting one or more β-lactamase enzyme comprising administering a combination of compound 1, or a pharmaceutically acceptable salt thereof, and sulbactam, or a pharmaceutically acceptable salt thereof, to an animal in need thereof. In a further aspect, the one or more β-lactamase enzyme is a serine β-lactamase enzyme. In a further aspect, the one or more β-lactamase enzyme is selected from the group consisting of Class A, Class C and Class D. In a further aspect, the one or more β-lactamase enzyme is a Class A enzyme. In a further aspect, the one or more β-lactamase enzyme is a Class C enzyme. In a further aspect, the one or more β-lactamase enzyme is a Class D enzyme. In a further aspect, the one or more β-lactamase enzyme is a Class D enzyme and one or more of Class A and C enzymes.

In one aspect, there is provided a combination of compound 1, or a pharmaceutically acceptable salt thereof, and sulbactam, or a pharmaceutically acceptable salt for use in treating a bacterial infection in a warm-blooded animal, such as man.

In one aspect, there is provided a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in treating a bacterial infection in a warm-blooded animal, such as man.

In another aspect, there is provided a combination of compound 1, or a pharmaceutically acceptable salt thereof, and sulbactam, or a pharmaceutically acceptable salt thereof, for use in treating urinary tract infections, pneumonia (including HAP and VAP), bacteremia, meningitis and/or wound and surgical site infections, in a warm-blooded animal such as man.

In yet another aspect, there is provided a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in treating urinary tract infections, pneumonia (including HAP and VAP), bacteremia, and/or skin and skin-structure infections, in a warm-blooded animal, such as man.

In one embodiment, the invention is compound 1, or a pharmaceutically acceptable salt thereof, for use in the treatment of a bacterial infection, wherein the treatment is performed in combination with sulbactam, or a pharmaceutically acceptable salt thereof, in a patient who is not being treated with any additional antibiotics or β-lactamase inhibitors, such as, for example, aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, vancomycin, tazobactam, avibactam, clavulonic acid, LK-157, LK-176, SA-1-204, SA-2-13, BLI-489 (Pfizer/Wyeth), BAL0029880 (Baselea) and/or relebactam (MK7655).

In one embodiment, the invention is sulbactam, or a pharmaceutically acceptable salt thereof, for use in the treatment of a bacterial infection, wherein the treatment is performed in combination with compound 1, or a pharmaceutically acceptable salt thereof, in a patient who is not being treated with any additional antibiotics or β-lactamase inhibitors, such as, for example, aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, vancomycin, tazobactam, avibactam, clavulonic acid, LK-157, LK-176, SA-1-204, SA-2-13, BLI-489 (Pfizer/Wyeth), BAL0029880 (Baselea) and/or relebactam (MK7655).

In one embodiment, the invention is compound 1, or a pharmaceutically acceptable salt thereof, for use in the treatment of a bacterial infection, wherein the treatment is performed in combination with sulbactam, or a pharmaceutically acceptable salt thereof, and imipenem, or a pharmaceutically acceptable salt thereof, and cilastatin, or a pharmaceutically acceptable salt thereof, in a patient who is not being treated with any additional antibiotics or β-lactamase inhibitors, such as, for example, aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, vancomycin, tazobactam, avibactam, clavulonic acid, LK-157, LK-176, SA-1-204, SA-2-13, BLI-489 (Pfizer/Wyeth), BAL0029880 (Baselea) and/or relebactam (MK7655).

Compound 1, or a pharmaceutically acceptable salt thereof, may be administered to a subject by any one of several different routes of administration. In some embodiments, compound 1, or a pharmaceutically acceptable salt thereof, is administered to a subject systemically. In other embodiments, compound 1, or a pharmaceutically acceptable salt thereof, is administered to a subject locally. In some embodiments, compound 1, or a pharmaceutically acceptable salt thereof, is administered to a subject parenterally. In some embodiments, compound 1, or a pharmaceutically acceptable salt thereof, is administered to a subject intravenously.

In some embodiments, sulbactam, or a pharmaceutically acceptable salt thereof, is administered to a subject systemically. In other embodiments, sulbactam, or a pharmaceutically acceptable salt thereof, is administered to a subject locally. In some embodiments, sulbactam, or a pharmaceutically acceptable salt thereof, is administered to a subject parenterally. In some embodiments, sulbactam, or a pharmaceutically acceptable salt thereof, is administered to a subject intravenously. In any of these embodiments, an effective amount of sulbactam, or a pharmaceutically acceptable salt thereof, is obtained by administering an amount of the combination Unasyn®, Cefina-SB®, Sulperazone®, Sultamicillin® or Bacperazone®, which provides an effective dose of sulbactam. The route of administration for any of the combination products Unasyn®, Cefina-SB®, Sulperazone®, Sultamicillin® or Bacperazone® is as is approved for each.

In some embodiments, imipenem/cilastatin, or pharmaceutically acceptable salts thereof, are administered to a subject systemically. In other embodiments, imipenem/cilastatin, or pharmaceutically acceptable salts thereof, are administered to a subject locally. In some embodiments, imipenem/cilastatin, or pharmaceutically acceptable salts thereof, are administered to a subject parenterally. In some embodiments, imipenem/cilastatin, or pharmaceutically acceptable salts thereof, are administered to a subject intravenously. In any of these embodiments, an effective amount of imipenem/cilastatin, or pharmaceutically acceptable salts thereof, are obtained by administering an amount of the combination Primaxin®, which provides an effective dose of both imipenem and cilastatin. The route of administration for the Primaxin® product may be as any and all routes currently approved for it.

Intravenous delivery of compound 1, or a pharmaceutically acceptable salt thereof, and/or sulbactam, or a pharmaceutically acceptable salt thereof, optionally in combination with imipenem/cilastatin, may provide the greatest flexibility in dosing with the fewest logistical barriers to development. For example, dosing of intravenous compound 1, or a pharmaceutically acceptable salt thereof, sulbactam, or a pharmaceutically acceptable salt thereof, and optionally imipenem/cilastatin, can be titrated to effect, or withdrawn if a particular patient experiences a side effect. In some embodiments, the compound 1, or a pharmaceutically acceptable salt thereof, sulbactam, or a pharmaceutically acceptable salt thereof, and optionally imipenem/cilastatin is administered at one site of a subject's body and the antibacterial effect is observed at a different site of the subject's body (e.g., systemic effects are observed following delivery).

The terms "treatment", "treating", and the like are used herein to generally mean improvement in any symptoms associated with or caused by a Gram-positive or Gram-negative bacterial infection. "Treatment", as used herein, may refer to an improvement in any of the following: fever, inflammation, swelling, vomiting, fatigue, cramping, coughing, sneezing, respiratory illness, diarrhea, meningitis, headaches, joint pain, body aches, blisters, rashes, nausea, chills, dizziness, drowsiness, sleeplessness, gagging, skin irritation, excessive mucus production (e.g. in the eyes, gastrointestinal tract, sinuses, or respiratory system), ulcers, gastrointestinal discomfort, skin loss, hair loss, necrosis, and organ dysfunction. Improvements in any of these conditions can be readily assessed according to standard methods and techniques known in the art. The population of subjects treated by the method of the disease includes subjects suffering from the undesirable condition or disease, as well as subjects at risk for development of the condition or disease.

An "anti-bacterial response" is any detectable improvement in any of the following symptoms: fever, inflammation, swelling, vomiting, fatigue, cramping, coughing, sneezing, respiratory illness, diarrhea, meningitis, headaches, joint pain, body aches, blisters, rashes, nausea, chills, dizziness, drowsiness, sleeplessness, gagging, skin irritation, excessive mucus production (e.g. in the eyes, gastrointestinal tract, sinuses, or respiratory system), ulcers, skin loss, hair loss, necrosis, and organ dysfunction. In some embodiments, an anti-bacterial response is achieved in a subject suffering from a bacterial infection following the administration of less than or equal to one to four daily doses of compound 1, or a pharmaceutically acceptable salt thereof, and sulbactam, or a pharmaceutically acceptable salt thereof, as described herein for the duration of treatment. Subjects suffering from a bacterial infection, or healthy control subjects, may be assessed before and after treatment with a combination of compound 1, or a pharmaceutically acceptable salt thereof, and sulbactam, or a pharmaceutically acceptable salt thereof, by using any one of, or combination of, numerous different standards or scales employed by a person having ordinary skill in the art. Examples of standards or scales for testing the effectiveness of the methods disclosed herein include assessment of body temperature, body weight, Lab-Score, procalcitonin levels, circulating white blood cell levels, Laboratory Risk Indicator for Necrotizing Fasciitis (LRINEC) score, mucus levels, urea breath test, or levels of bacteria present in a sample taken from a subject (e.g., blood, serum, mucus, skin, stool, urine, sputum, saliva, semen, or biopsy sample).

In a first embodiments, compound 1, or a pharmaceutically acceptable salt thereof, and sulbactam, or a pharmaceutically acceptable salt thereof, and optionally imipenem/cilastatin, or pharmaceutically acceptable salts thereof, are administered to a subject with a bacterial infection concurrently. In a second embodiment, the first dose of compound 1, or a pharmaceutically acceptable salt thereof, is administered to a subject with a bacterial infection at a point after the administration to the subject of at least a first dose of sulbactam, or a pharmaceutically acceptable salt thereof. In a third embodiment, the first dose of sulbactam, or a pharmaceutically acceptable salt thereof, is administered to a subject with a bacterial infection at a point after the administration to the subject of at least a first dose of compound 1, or a pharmaceutically acceptable salt thereof. In a fourth embodiment, the first dose of compound 1, or a pharmaceutically acceptable salt thereof, is administered after achieving an anti-bacterial response associated with the administration of at least a first dose of sulbactam, or a pharmaceutically acceptable salt thereof. In any of these embodiments, the sulbactam can be administered as part of the combination Unasyn®, Cefina-SB®, Sulperazone®, Sultamicillin® or Bacperazone®. In any of the second, third, or fourth embodiments, imipenem/cilastatin, or pharmaceutically acceptable salts thereof, may be administered with either compound 1 or sulbactam, or may be administered before or after administration of compound 1 or sulbactam, or in between the two.

In some embodiments, compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, are administered to a subject with a bacterial infection concurrently. In other embodiments, compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, are administered to a subject with a bacterial infection sequentially wherein at least one component of the four are delivered before or after the delivery of the other components of the quad combination. In any of these embodiments, the sulbactam can be administered as part of the combination Unasyn®, Cefina-SB®, Sulperazone®, Sultamicillin® or Bacperazone®.

In some embodiments, the first dose of compound 1, or a pharmaceutically acceptable salt thereof, and/or sulbactam, or a pharmaceutically acceptable salt thereof, and optionally imipenem/cilastatin, or pharmaceutically acceptable salts thereof, is administered to a subject with a bacterial infection after the subject has displayed signs or symptoms associated with the bacterial infection. In other embodiments, the first dose of compound 1, or a pharmaceutically acceptable salt thereof, and/or sulbactam, or a pharmaceutically acceptable salt thereof, and optionally imipenem/cilastatin, or pharmaceutically acceptable salts thereof, is administered to a subject with a bacterial infection before the subject displays any signs or symptoms associated with the bacterial infection but after the patient has been, or is believed to have been, infected with a relevant pathogenic bacterial strain(s). In other embodiments, the first dose of compound 1, or a pharmaceutically acceptable salt thereof, and/or sulbactam, or a pharmaceutically acceptable salt thereof, and optionally imipenem/cilastatin, or pharmaceutically acceptable salts thereof, is administered to a subject with a bacterial infection before the subject displays any signs or symptoms associated with the bacterial infection but after the patient has been potentially exposed to a pathogenic bacterial strain(s) in a health care setting, such as prophylactic administration of the combination after a surgical procedure. Examples of signs or symptoms associated with a bacterial infection include fever, inflammation, swelling, vomiting, fatigue, cramping, coughing, sneezing, respiratory illness, diarrhea, meningitis, headaches, joint pain, body aches, blisters, rashes, nausea, chills, dizziness, drowsiness, sleeplessness, gagging, skin irritation, excessive mucus production (e.g. in the eyes, gastrointestinal tract, sinuses, or respiratory system), ulcers, skin loss, hair loss, necrosis, and organ dysfunction.

Methods of treating include administering to a subject with a bacterial infection compound 1, or a pharmaceutically acceptable salt thereof, sulbactam, or a pharmaceutically acceptable salt thereof, and optionally imipenemn/cilastatin, or pharmaceutically acceptable salts thereof, according to a dosing regimen. In some embodiments, the dosing regiment involves the administration of compound 1, or a pharmaceutically acceptable salt thereof, sulbactam, or a pharmaceutically acceptable salt thereof, and optionally imipenemn/cilastatin, or pharmaceutically acceptable salts thereof, according to a single dose or multiple doses. Multiple doses include administering compound 1, or a pharmaceutically acceptable salt thereof, sulbactam, or a pharmaceutically acceptable salt thereof, and optionally imipenemn/cilastatin, or pharmaceutically acceptable salts thereof, at specified intervals, such as once a day (once every about 24 hours), twice a day (once every about twelve hours), three times a day (once every about eight hours) or four times a day (once every about 6 hours). In some embodiments, compound 1, or a pharmaceutically acceptable salt thereof, sulbactam, or a pharmaceutically acceptable salt thereof, and optionally imipenemn/cilastatin, or pharmaceutically acceptable salts thereof, is administered to the subject with a bacterial infection at least once every eight hours. In some embodiments, compound 1, or a pharmaceutically acceptable salt thereof, sulbactam, or a pharmaceutically acceptable salt thereof, and optionally imipenemn/cilastatin, or pharmaceutically acceptable salts thereof, is administered to the subject with a bacterial infection at least once every six hours. In some embodiments, compound 1, or a pharmaceutically acceptable salt thereof, sulbactam, or a pharmaceutically acceptable salt thereof, and optionally imipenemn/cilastatin, or pharmaceutically acceptable salts thereof, is administered to the subject with a bacterial infection at least once every twelve hours. In other embodiments, the methods described herein comprise administering compound 1, or a pharmaceutically acceptable salt thereof, sulbactam, or a pharmaceutically acceptable salt thereof, and optionally imipenemn/cilastatin, or pharmaceutically acceptable salts thereof, to the subject until the subject is asymptomatic for bacterial infection(s). In one embodiment, about 300 mg to about 1000 mg of compound 1, or a pharmaceutically acceptable salt thereof, about 500 mg to about 1500 mg of sulbactam, or a pharmaceutically acceptable salt thereof, and optionally about 250 mg to about 500 mg of imipenem, or a pharmaceutically acceptable salt thereof, and about 250 mg to about 500 mg cilastatin, or a pharmaceutically acceptable salt thereof, is administered to the subject with a bacterial infection at least once every six hours. In one embodiment, about 500 mg of compound 1, or a pharmaceutically acceptable salt thereof, about 1000 mg of sulbactam, or a pharmaceutically acceptable salt thereof, about 500 mg of imipenem, or a pharmaceutically acceptable salt thereof, and about 500 mg of cilastatin, or a pharmaceutically acceptable salt thereof, is administered to the subject with a bacterial infection at least once every six hours. In one embodiment, about 500 mg of compound 1, or a pharmaceutically acceptable salt thereof, about 1000 mg of sulbactam, or a pharmaceutically acceptable salt thereof, and optionally about 1000 mg of imipenem, or a pharmaceutically acceptable salt thereof, and about 1000 mg of cilastatin, or a pharmaceutically acceptable salt thereof, is administered to the subject with a bacterial infection at least once every six hours.

A combination or pharmaceutical composition "consisting of" the β-lactamase inhibitor compound 1, or a pharmaceutically acceptable salt thereof, and sulbactam, or a pharmaceutically acceptable salt thereof, means combinations and pharmaceutical compositions wherein the only pharmaceutically active ingredients are compound 1, or a pharmaceutically acceptable salt thereof, and sulbactam and pharmaceutically acceptable salts thereof. Such combinations and compositions which consist of compound 1 or a pharmaceutically acceptable salt thereof, and sulbactam, or a pharmaceutically acceptable salt thereof, may optionally further comprise pharmaceutically inactive ingredients such as excipients, diluents, stabilizers, solubilizers, buffers, surfactants, and the like. Combination and compositions which consist of compound 1, or a pharmaceutically acceptable salt thereof, and sulbactam, or a pharmaceutically acceptable salt thereof, may contain the sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®.

A combination or pharmaceutical composition "consisting essentially of" the β-lactamase inhibitor compound 1, or a pharmaceutically acceptable salt thereof, and sulbactam, or a pharmaceutically acceptable salt thereof, means combinations and pharmaceutical compositions wherein the only β-lactamase inhibitor present is compound 1, or a pharmaceutically acceptable salt thereof, and the only compound with antibiotic activity present is sulbactam, or a pharmaceutically acceptable salt thereof. Such combinations and compositions, which consist essentially of compound 1 or a pharmaceutically acceptable salt thereof, and sulbactam, or a pharmaceutically acceptable salt thereof, may optionally further comprise other pharmaceutically active agents which are not a β-lactamase inhibitor or compounds with antibiotic activity (e.g., antifungal agents, anthistimines, antiinflammtory compounds, etc.), as well as inactive ingredients such as excipients, diluents, stabilizers, solubilizers, buffers, surfactants, and the like. Combination and compositions, which consist essentially of compound 1 or a pharmaceutically acceptable salt thereof, and sulbactam, or a pharmaceutically acceptable salt thereof, may contain the sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®.

In one embodiment, a combination consisting essentially of, or consisting of, the β-lactamase inhibitor compound 1, or a pharmaceutically acceptable salt thereof, and sulbactam, or a pharmaceutically acceptable salt thereof, may optionally contain one or more pharmaceutically acceptable carriers, diluents and/or excipients, and optionally ampicillin or cefoperazone.

A combination or pharmaceutical composition "consisting of" the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, means combinations and pharmaceutical compositions wherein the only pharmaceutically active ingredients are compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof. Such combinations and compositions which consist of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may optionally further comprise pharmaceutically inactive ingredients such as excipients, diluents, stabilizers, solubilizers, buffers, surfactants, and the like. Combination and compositions which consist of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may contain the sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®, and/or may contain the imipenem/cilastatin, or pharmaceutically acceptable salts thereof, in form of the product Primaxin®.

A combination or pharmaceutical composition "consisting essentially of" the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, means combinations and pharmaceutical compositions wherein the only β-lactamase inhibitor present is compound 1, or a pharmaceutically acceptable salt thereof, and the only compounds with antibiotic activity present are sulbactam, or a pharmaceutically acceptable salt thereof, and imipenem, or a pharmaceutically acceptable salt thereof, along with an amount of cilastatin, or a pharmaceutically acceptable salt thereof, to allow the imipenem to have a sufficient antibiotic effect. Such combinations and compositions, which consist essentially of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may optionally further comprise other pharmaceutically active agents which are not a β-lactamase inhibitor or compounds with antibiotic activity (e.g., antifungal agents, anthistimines, antiinflammtory compounds, etc.), as well as inactive ingredients such as excipients, diluents, stabilizers, solubilizers, buffers, surfactants, and the like. Combination and compositions, which consist essentially of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may contain the sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®, and/or may contain the imipenem/cilastatin, or pharmaceutically acceptable salts thereof, in form of the product Primaxin®.

In one embodiment, a combination consisting essentially of, or consisting of, the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may optionally contain one or more pharmaceutically acceptable carriers, diluents and/or excipients, and optionally ampicillin or cefoperazone.

Methods of treating a bacterial infection in a subject in need thereof, "consisting essentially of" administering to the subject in need thereof an effective amount of the β-lactamase inhibitor compound 1, or a pharmaceutically acceptable salt thereof, and sulbactam, or a pharmaceutically acceptable salt thereof, means administration of combinations and pharmaceutical compositions wherein the only β-lactamase inhibitor present is compound 1, or a pharmaceutically acceptable salt thereof, and the only compound with antibiotic activity present is sulbactam, or a pharmaceutically acceptable salt thereof. Methods of treating a bacterial infection in subjects in need thereof by administering combinations and compositions which consist essentially of compound 1 or a pharmaceutically acceptable salt thereof, and sulbactam, or a pharmaceutically acceptable salt thereof, may optionally include administration of other pharmaceutically active agents which are not a β-lactamase inhibitor or compounds with antibiotic activity (e.g., antifungal agents, anthistimines, antiinflammtory compounds, etc.). Methods of treating a bacterial infection in subjects in need thereof by administering combinations and compositions which consist essentially of compound 1 or a pharmaceutically acceptable salt thereof, and sulbactam, or a pharmaceutically acceptable salt thereof, may provide that the sulbactam, or pharmaceutically acceptable salt thereof, is administered in the form of a sulbactam+ampicillin or cefoperazone combination product, such as Unasyn®, Cefina-SB®, Sulperazone®, Sultamicillin® or Bacperazone®.

Methods of treating a bacterial infection in a subject in need thereof, "consisting of" administering to the subject in need thereof an effective amount of the β-lactamase inhibitor compound 1, or a pharmaceutically acceptable salt thereof, and sulbactam, or a pharmaceutically acceptable salt thereof, means administration of combinations and pharmaceutical compositions wherein the only pharmaceutically active agents being administered to the patient are the β-lactamase inhibitor compound 1, or a pharmaceutically acceptable salt thereof, and the compound with antibiotic activity sulbactam, or a pharmaceutically acceptable salt thereof. Administration of any pharmaceutically active agent requires administration of them in an appropriate pharmaceutical composition, which typically includes administration of inactive ingredients required for formulation. Methods of treating a bacterial infection in a subject in need thereof, "consisting of" administering to the subject in need thereof an effective amount of the β-lactamase inhibitor compound 1, or a pharmaceutically acceptable salt thereof, and sulbactam, or a pharmaceutically acceptable salt thereof, includes administration of any and all inactive ingredients required for the formulation of the active agents. Methods of treating a bacterial infection in subjects in need thereof by administering combinations and compositions which "consist of" compound 1 or a pharmaceutically acceptable salt thereof, and sulbactam, or a pharmaceutically acceptable salt thereof, may provide that the sulbactam, or pharmaceutically acceptable salt thereof, is administered in the form of a sulbactam+ampicillin or cefoperazone combination product, such as Unasyn®, Cefina-SB®, Sulperazone®, Sultamicillin® or Bacperazone®.

Methods of treating a bacterial infection in a subject in need thereof, "consisting essentially of" administering to the subject in need thereof an effective amount of the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, means administration of combinations and pharmaceutical compositions wherein the only β-lactamase inhibitor present is compound 1, or a pharmaceutically acceptable salt thereof, and the only compounds with antibiotic activity present are sulbactam, or a pharmaceutically acceptable salt thereof, and imipenem, or a pharmaceutically acceptable salt thereof, along with an amount of cilastatin which allows imipenem to achieve the desired antibacterial effect. Methods of treating a bacterial infection in subjects in need thereof by administering combinations and compositions which consist essentially of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may optionally include administration of other pharmaceutically active agents which are not a β-lactamase inhibitor or compounds with antibiotic activity (e.g., antifungal agents, anthistimines, antiinflammtory compounds, etc.). Methods of treating a bacterial infection in subjects in need thereof by administering combinations and compositions which consist essentially of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may provide that the sulbactam, or pharmaceutically acceptable salt thereof, is administered in the form of a sulbactam+ampicillin or cefoperazone combination product, such as Unasyn®, Cefina-SB®, Sulperazone®, Sultamicillin® or Bacperazone®, and/or may provide the imipenem/cilastatin, or pharmaceutically acceptable salts thereof, in the form of the Primaxin® product.

Methods of treating a bacterial infection in a subject in need thereof, "consisting of" administering to the subject in need thereof an effective amount of the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, means administration of combinations and pharmaceutical compositions wherein the only pharmaceutically active agents being administered to the patient are the β-lactamase inhibitor compound 1, or a pharmaceutically acceptable salt thereof, and the compounds with antibiotic activity are sulbactam, or a pharmaceutically acceptable salt thereof and imipenem, or a pharmaceutically acceptable salt thereof, in addition to an amount of cilastatin, or a pharmaceutically acceptable salt thereof, which allows imipenem to achieve the desired antibacterial effect. Administration of any pharmaceutically active agent requires administration of them in an appropriate pharmaceutical composition, which typically includes administration of inactive ingredients required for formulation. Methods of treating a bacterial infection in a subject in need thereof, "consisting of" administering to the subject in need thereof an effective amount of the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, includes administration of any and all inactive ingredients required for the formulation of the active agents. Methods of treating a bacterial infection in subjects in need thereof by administering combinations and compositions which "consist of" compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, may provide that the sulbactam, or pharmaceutically acceptable salt thereof, is administered in the form of a sulbactam+ampicillin or cefoperazone combination product, such as Unasyn®, Cefina-SB®, Sulperazone®, Sultamicillin® or Bacperazone®, and/or may provide the imipenem/cilastatin, or pharmaceutically acceptable salts thereof, in the form of the Primaxin® product.

A combination or pharmaceutical composition "consisting of" the β-lactamase inhibitor compound 1, or a pharmaceutically acceptable salt thereof, and sulbactam, or a pharmaceutically acceptable salt thereof, for use in the treatment of a bacterial infection, includes combinations and pharmaceutical compositions wherein the only pharmaceutically active ingredients are compound 1, or a pharmaceutically acceptable salt thereof, and sulbactam and pharmaceutically acceptable salts thereof. Use of any compound for treatment of any disease requires the presence of all pharmaceutically active agent(s) in an appropriate pharmaceutical composition, which typically also includes any and all inactive ingredients required for formulation. Combinations and compositions which "consist of" compound 1, or a pharmaceutically acceptable salt thereof, and sulbactam, or a pharmaceutically acceptable salt thereof, for use in the treatment of a bacterial infection therefore includes any inactive ingredients such as excipients, diluents, stabilizers, solubilizers, buffers, surfactants, and the like present in the formulation of compound 1 and sulbactam. Combination and compositions which "consist of" compound 1, or a pharmaceutically acceptable salt thereof, and sulbactam, or a pharmaceutically acceptable salt thereof, for use in the treatment of a bacterial infection optionally includes sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®.

A combination or pharmaceutical composition "consisting essentially of" the β-lactamase inhibitor compound 1, or a pharmaceutically acceptable salt thereof, and sulbactam, or a pharmaceutically acceptable salt thereof, for use in the treatment of bacterial infections means combinations and pharmaceutical compositions wherein the only β-lactamase inhibitor present is compound 1, or a pharmaceutically acceptable salt thereof, and the only compound with antibiotic activity present is sulbactam, or a pharmaceutically acceptable salt thereof. Use of combinations and compositions which "consist essentially of" compound 1 or a pharmaceutically acceptable salt thereof, and sulbactam, or a pharmaceutically acceptable salt thereof, for the treatment of bacterial infections may optionally comprise other pharmaceutically active agents which are not a β-lactamase inhibitor or compounds with antibiotic activity (e.g., antifungal agents, anthistimines, antiinflammtory compounds, etc.), as well as inactive ingredients such as excipients, diluents, stabilizers, solubilizers, buffers, surfactants, and the like. Combination and compositions, which consist essentially of compound 1 or a pharmaceutically acceptable salt thereof, and sulbactam, or a pharmaceutically acceptable salt thereof, for use in the treatment of bacterial infections may include sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®.

A combination or pharmaceutical composition "consisting of" the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of a bacterial infection, means combinations and pharmaceutical compositions wherein the only pharmaceutically active ingredients are compound 1, or a pharmaceutically acceptable salt thereof, sulbactam and pharmaceutically acceptable salts thereof, imipenem, or a pharmaceutically acceptable salt thereof, and cilastatin, or a pharmaceutically acceptable salt thereof. Use of any compound for treatment of any disease requires the presence of all pharmaceutically active agent(s) in an appropriate pharmaceutical composition, which typically includes any and all inactive ingredients required for formulation. Combinations and compositions which "consist of" compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of a bacterial infection therefore includes any inactive ingredients such as excipients, diluents, stabilizers, solubilizers, buffers, surfactants, and the like present in the formulation of compound 1, sulbactam, imipenem and cilastatin. Combination and compositions which "consist of" compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of a bacterial infection includes sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®, and may further also include the imipenem/cilastatin in the form of the Primaxin® product.

A combination or pharmaceutical composition "consisting essentially of" the β-lactamase inhibitor compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of bacterial infections means combinations and pharmaceutical compositions wherein the only β-lactamase inhibitor present is compound 1, or a pharmaceutically acceptable salt thereof, the only compounds with antibiotic activity present are sulbactam, or a pharmaceutically acceptable salt thereof, and imipenem, or a pharmaceutically acceptable salt thereof, in combination with an effective amount of cilastatin, or a pharmaceutically acceptable salt thereof, which allows the imipenem to have a sufficient antibacterial effect. Use of combinations and compositions which "consist essentially of" compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for the treatment of bacterial infections may optionally comprise other pharmaceutically active agents which are not a β-lactamase inhibitor or compounds with antibiotic activity (e.g., antifungal agents, antihistimines, antiinflammtory compounds, etc.), as well as inactive ingredients such as excipients, diluents, stabilizers, solubilizers, buffers, surfactants, and the like. Combination and compositions, which consist essentially of compound 1 or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, for use in the treatment of bacterial infections may include the sulbactam, or pharmaceutically acceptable salt thereof, in the form of a sulbactam+ampicillin or cefoperazone combination product, such as Unasyn®, Cefina-SB®, Sulperazone®, Sultamicillin® or Bacperazone®, and may further also include the imipenem/cilastatin in the form of the Primaxin® product.

In one embodiment, a combination or pharmaceutical composition which "consists essentially of" compound 1, or a pharmaceutically acceptable salt thereof, sulbactam, or a pharmaceutically acceptable salt thereof, and optionally imipenem/cilastatin, or pharmaceutically acceptable salts thereof, may not contain any additional antibiotic agents or β-lactamase inhibitors such as aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, vancomycin, tazobactam, avibactam, clavulinic acid, LK-157, LK-176, SA-1-204, SA-2-13, BLI-489 (Pfizer/Wyeth), BAL0029880 (Baselea) and/or relebactam (MK-7655).

In still another aspect, there is provided a pharmaceutical composition comprising a combination of compound 1, or a pharmaceutically acceptable salt thereof, and sulbactam, or a pharmaceutically acceptable salt thereof, and at least one pharmaceutically acceptable carrier, diluent, and/or excipient. In still another aspect, there is provided a pharmaceutical composition comprising a combination of about 500 mg of compound 1, or a pharmaceutically acceptable salt thereof, and about 1000 mg of sulbactam, or a pharmaceutically acceptable salt thereof, and at least one pharmaceutically acceptable carrier, diluent, and/or excipient.

In still another aspect, there is provided a pharmaceutical composition comprising a combination of compound 1, or a pharmaceutically acceptable salt thereof, sulbactam, or a pharmaceutically acceptable salt thereof, imipenem, or a pharmaceutically acceptable salt thereof, and cilastatin, or a pharmaceutically acceptable salt thereof, and at least one pharmaceutically acceptable carrier, diluent, and/or excipient. In still another aspect, there is provided a pharmaceutical composition comprising a combination of about 500 mg of compound 1, or a pharmaceutically acceptable salt thereof, about 1000 mg of sulbactam, or a pharmaceutically acceptable salt thereof, about 500 mg imipenem, or a pharmaceutically acceptable salt thereof, and about 500 mg cilastatin, or a pharmaceutically acceptable salt thereof, and at least one pharmaceutically acceptable carrier, diluent, and/or excipient. In still another aspect, there is provided a pharmaceutical composition comprising a combination of about 500 mg of compound 1, or a pharmaceutically acceptable salt thereof, about 1000 mg of sulbactam, or a pharmaceutically acceptable salt thereof, about 1000 mg imipenem, or a pharmaceutically acceptable salt thereof, and about 1000 mg cilastatin, or a pharmaceutically acceptable salt thereof, and at least one pharmaceutically acceptable carrier, diluent, or excipient.

Various delivery systems are known and can be used to administer compound 1, or a pharmaceutically acceptable salt thereof, and/or sulbactam, or a pharmaceutically acceptable salt thereof, and optionally imipenem/cilastatin, or pharmaceutically acceptable salts thereof, of the disclosure, e.g., various formulations, encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, and oral (for example as tablets, lozenges, hard or soft capsules, aqueous or oily suspensions, emulsions, dispersible powders or granules, syrups or elixirs), inhalation (for example as a finely divided powder or a liquid aerosol), insufflation (for example as a finely divided powder). In particular embodiments, parenteral introduction includes intramuscular, subcutaneous, intravenous, intravascular, as a suppository for rectal dosing, and intrapericardial administration.

Administration may be systemic or local. The present disclosure provides systemic delivery of one or more doses of compound 1, or a pharmaceutically acceptable salt thereof, and/or sulbactam, or a pharmaceutically acceptable salt thereof, and optionally imipenem/cilastatin, or pharmaceutically acceptable salts thereof, of the disclosure. Systemic delivery includes, for example, subcutaneous, intravenous, or intramuscular.

The compound 1, or a pharmaceutically acceptable salt thereof, and/or sulbactam, or a pharmaceutically acceptable salt thereof, and optionally imipenem/cilastatin, or pharmaceutically acceptable salts thereof, may be administered by any convenient route, for example, by infusion or bolus injection.

In certain embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are administered by intravenous infusion. In certain embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about five minutes to about four hours. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about an hour. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about two hours. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about three hours. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about five to about thirty minutes. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about thirty minutes to about an hour. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about two hours to about three hours. In other embodiments, the compound 1, or a pharmaceutically acceptable salt thereof, and/or sulbactam, or a pharmaceutically acceptable salt thereof, and optionally imipenem/cilastatin, or pharmaceutically acceptable salts thereof, are infused over a period of about two and a half hours to about three hours.

In one embodiment, about 500 mg of compound 1, or a pharmaceutically acceptable salt thereof, and/or about 1000 mg of sulbactam, or a pharmaceutically acceptable salt thereof, is administered to the subject with a bacterial infection at least once every six hours, wherein the infusion is administered over a period of approximately three hours.

In one embodiment, about 500 mg of compound 1, or a pharmaceutically acceptable salt thereof, about 1000 mg of sulbactam, or a pharmaceutically acceptable salt thereof, about 500 mg imipenem, or a pharmaceutically acceptable salt thereof, and about 500 mg cilastatin, or a pharmaceutically acceptable salt thereof, is administered to the subject with a bacterial infection at least once every six hours, wherein the infusion is administered over a period of approximately three hours.

In one embodiment, about 500 mg of compound 1, or a pharmaceutically acceptable salt thereof, about 1000 mg of sulbactam, or a pharmaceutically acceptable salt thereof, about 1000 mg imipenem, or a pharmaceutically acceptable salt thereof, and about 1000 mg cilastatin, or a pharmaceutically acceptable salt thereof, is administered to the subject with a bacterial infection at least once every six hours, wherein the infusion is administered over a period of approximately three hours.

In some embodiments, compound 1, or a pharmaceutically acceptable salt thereof, and sulbactam, or a pharmaceutically acceptable salt thereof, are administered in the same formulation. In other embodiments, compound 1, or a pharmaceutically acceptable salt thereof, and sulbactam, or a pharmaceutically acceptable salt thereof, are administered in separate formulations. In some embodiments, the compound 1, or a pharmaceutically acceptable salt thereof, and sulbactam, or a pharmaceutically acceptable salt thereof, are administered to a subject suffering from a bacterial infection concurrently. In some embodiments, compound 1, or a pharmaceutically acceptable salt thereof, and sulbactam, or a pharmaceutically acceptable salt thereof, are administered to a subject suffering from a bacterial infection consecutively. In some embodiments, compound 1, or a pharmaceutically acceptable salt thereof, and sulbactam, or a pharmaceutically acceptable salt thereof, are administered via the same route of administration. In some embodiments, compound 1, or a pharmaceutically acceptable salt thereof, and sulbactam, or a pharmaceutically acceptable salt thereof, are administered on different dosing schedules and/or via different routes of administration. In some embodiments, the first dose of compound 1, or a pharmaceutically acceptable salt thereof, is administered to a subject suffering from a bacterial infection at a point after the administration to the subject of at least a first dose of sulbactam, or a pharmaceutically acceptable salt thereof. In other embodiments, the first dose of sulbactam, or a pharmaceutically acceptable salt thereof, is administered to a subject suffering from a bacterial infection at a point after the administration to the subject of at least a first dose of compound 1, or a pharmaceutically acceptable salt thereof. In some embodiments, the first dose of sulbactam, or a pharmaceutically acceptable salt thereof, is administered after achieving an initial anti-bacterial response associated with the administration of at least a first dose of compound 1, or a pharmaceutically acceptable salt thereof. In other embodiments, the first dose of compound 1, or a pharmaceutically acceptable salt thereof, is administered after achieving an initial anti-bacterial response associated with the administration of at least a first dose of sulbactam, or a pharmaceutically acceptable salt thereof.

In any of the above embodiments, the sulbactam component of the claimed combination, or pharmaceutically acceptable salt thereof, may be administered by administering the combination product marketed as Unasyn®, Cefina-SB®, Sulperazone®, Sultamicillin® or Bacperazone®.

The compositions of the invention may be obtained by conventional procedures using conventional pharmaceutical excipients well known in the art. Thus, compositions intended for oral use may contain, for example, one or more coloring, sweetening, flavoring and/or preservative agents.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

The amount of active ingredient that is combined with one or more excipients to produce a single dosage form will necessarily vary depending upon the host treated and the particular route of administration. For example, a formulation intended for administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 1000 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. Accordingly, the optimum dosage may be determined by the practitioner who is treating any particular patient.

Compound 1 as set forth above can be achieved by methods well-known in the art. For example, the synthesis of compound 1 is set forth in example 10 of WO 13/150296, the contents of which are incorporated herein by reference. Sulbactam and its pharmaceutically acceptable salts, is commercially available in the form of the combination Unasyn®, Cefina-SB®, Sulperazone®, Sultamicillin® or Bacperazone®. Synthesis of sulbactam is also well-known in the art. See, for example, Volkmann, et al., *Efficient Preparation of 6,6-dihalopenicillanic acids. Synthesis of Penicillanic Acid S,S-dixoide (Sulbactam)*, J. Org. Chem., 47(17):3344-3345 (1982), the contents of which are incorporated by reference herein.

EXAMPLES

Example 1: Biological Activity of Sulbactam v. Unasyn®

Minimum Inhibitory Concentrations (MICs) were determined by the broth microdilution method in accordance with the Clinical and Laboratory Standards Institute (CLSI) guidelines. Clinical Laboratory Standards Institute: Methods for Dilution Antimicrobial Susceptability Tests for Bacteria That Grow Aerobically ($10^{th}$ Ed. (2015)) M07-A10. Activity of sulbactam was assessed against a panel of *A. baumannii* (n=60) clinical isolates. The panels were enriched with β-lactam-resistant isolates, caused by a variety of β-lactamases of all classes (A, B, C, and D). MICs were determined according to CLSI guidelines, and MIC50 and MIC90 values were calculated for the isolate populations. Following incubation, the lowest concentration of the drug that prevented visible growth was recorded as the MIC. Performance of the assay was monitored by the use of laboratory quality-control strains and commercially available control compounds with defined MIC spectrums, in accordance with CLSI guidelines.

Sixty geographically diverse strains of *A. baumannii* from recent (post-2006) nosocomial infections were tested for their susceptibility to sulbactam alone, Unasyn® (sulbactam:ampicillin in a 1:2 ratio) and five control compounds. As shown in Table 1, the inherent antibacterial activity of sulbactam against these strains ranged from 0.5 to >64 μg/ml. Unasyn® was about two-fold less effective with a range of activity from 1 to >32 μg/ml. This demonstrates the antibacterial activity of Unasyn is due to the sulbactam component, in agreement with previous studies as illustrated when a comparison of the number of susceptible strains to either drug at each concentration tested was made (FIG. 1).

TABLE 1

Sulbactam shows a wide range of activity against recent clinical strains of *A. baumanii*. Minimal inhibitory concentration (MIC) in μg/mL of each of the following compounds is shown: SUL = sulbactam, UNA = Unasyn, a 2:1 combination of ampicillin and sulbactam, MEM = meropenem, COL = colistin, LEVO = levofloxacin, GENT = gentamycin and TET = tetracycline.

| strain | β-lactamase content | SUL | UNA | MEM | COL | LEVO | GENT | TET |
|---|---|---|---|---|---|---|---|---|
| ARC3491§ | OXA-215 | 0.5 | 1 | 2 | 0.5 | 1 | 2 | 4 |
| ARC593 | OXA-98 | 1 | 2 | 1 | 0.5 | 0.25 | 8 | 2 |
| ARC2582 | OXA* | 1 | 2 | 0.25 | 0.125 | 0.125 | 4 | 2 |
| ARC2597§ | OXA* | 1 | 2 | 0.125 | 0.125 | <0.03 | 0.25 | 1 |
| ARC2058 | OXA-95 | 2 | 2 | 0.25 | 0.5 | 0.125 | 1 | 1 |
| ARC2728§ | OXA* | 2 | 2 | 0.25 | 0.25 | 0.125 | 0.25 | 1 |
| ARC5090 | OXA* | 2 | 2 | 0.25 | 0.25 | 0.125 | 0.25 | 2 |
| ARC2719 | OXA* | 2 | 4 | 0.25 | 0.125 | 0.125 | 0.5 | 2 |
| ARC2720§ | OXA* | 2 | 4 | 1 | 0.125 | 2 | 0.5 | 2 |
| ARC3489 | OXA*; OXA-68 | 2 | 8 | 4 | 0.25 | 16 | >32 | >32 |
| ARC3494 | OXA-65 | 4 | 2 | 0.25 | 0.5 | 0.25 | 0.25 | 2 |

TABLE 1-continued

Sulbactam shows a wide range of activity against recent clinical strains of *A. baumanii*. Minimal inhibitory concentration (MIC) in µg/mL of each of the following compounds is shown: SUL = sulbactam, UNA = Unasyn, a 2:1 combination of ampicillin and sulbactam, MEM = meropenem, COL = colistin, LEVO = levofloxacin, GENT = gentamycin and TET = tetracycline.

| strain | β-lactamase content | SUL | UNA | MEM | COL | LEVO | GENT | TET |
|---|---|---|---|---|---|---|---|---|
| ARC2780§ | OXA*; OXA-2; IMP-1 | 4 | 4 | 32 | 4 | 4 | >32 | 2 |
| ARC3487 | OXA-20; OXA-58; OXA-66 | 4 | 8 | 8 | 0.25 | 8 | 8 | 16 |
| ARC3659 | OXA-23; OXA* | 4 | 8 | 8 | 0.25 | 8 | >32 | 8 |
| ARC5084 | IMP-4(B); OXA-58; OXA-65 | 4 | 8 | >32 | 0.125 | 4 | >32 | 2 |
| ARC2682 | SHV-5; OXA-113 | 4 | 16 | 32 | 0.25 | 16 | >32 | 8 |
| ARC2059 | PSE-2; PSE-1 | 8 | 16 | 0.5 | 0.25 | >32 | 1 | 4 |
| ARC5092 | OXA-23; OXA-64 | 8 | 16 | 16 | >32 | 8 | >32 | 32 |
| ARC3485 | OXA-82 | 8 | 32 | 16 | 0.25 | 16 | 1 | 32 |
| ARC2674 | SHV-5; OXA-113 | 8 | 32 | 8 | 0.25 | 16 | 8 | >32 |
| ARC2788 | OXA-65; TEM-1 | 8 | 32 | 1 | 0.125 | 32 | 16 | 4 |
| ARC3515 | OXA-64; OXA-58 | 8 | 32 | 4 | 0.25 | 8 | 4 | >32 |
| ARC5081 | OXA-94; OXA-23 | 8 | 32 | 16 | 0.125 | 8 | 0.25 | 2 |
| ARC5091 | OXA-82; OXA-23 | 8 | 32 | 32 | 8 | >32 | >32 | 32 |
| ARC2777 | OXA-172; TEM-1 | 8 | >32 | 32 | 0.5 | 32 | 16 | 32 |
| ARC3488 | OXA*; OXA-68 | 16 | 16 | 4 | 2 | 32 | >32 | >32 |
| ARC5075 | SHV-5; OXA-113 | 16 | 16 | 32 | 0.25 | 32 | >32 | >32 |
| ARC5088 | OXA-20; OXA-58; OXA-66 | 16 | 16 | 8 | 0.125 | 8 | 8 | 16 |
| ARC2675 | SHV-5; OXA-113 | 16 | 32 | >32 | 0.125 | 32 | >32 | 16 |
| ARC2681 | OXA-40; TEM-1; OXA-132 | 16 | 32 | 32 | 0.25 | 16 | >32 | >32 |
| ARC2778 | OXA-40; TEM-1; OXA-65 | 16 | 32 | >32 | 0.25 | 32 | >32 | >32 |
| ARC2779§ | OXA-2; VIM-2 | 16 | 32 | 16 | 0.25 | 0.125 | >32 | 2 |
| ARC3484 | TEM-1; OXA-23; OXA-64 | 16 | 32 | 32 | 0.125 | 8 | >32 | >32 |
| ARC3492 | OXA-40; OXA-132; TEM-1 | 16 | 32 | >32 | 0.25 | 8 | >32 | >32 |
| ARC3513 | TEM-1; OXA-23; OXA-65 | 16 | 32 | 32 | 1 | 16 | >32 | 8 |
| ARC5073 | OXA-23; TEM-1; OXA-64; PER-1 | 16 | 32 | >32 | 0.125 | 8 | 0.5 | >32 |
| ARC5083 | OXA-66; OXA-23 | 16 | 32 | 16 | 0.125 | >32 | >32 | >32 |
| ARC2461 | OXA-66; TEM-1 | 16 | >32 | 2 | 0.125 | 16 | >32 | >32 |
| ARC2462 | TEM-1; OXA-66 | 16 | >32 | 4 | 0.125 | 16 | >32 | >32 |
| ARC2598 | OXA*; TEM-1; OXA-113 | 16 | >32 | 8 | 0.25 | 4 | 2 | >32 |
| ARC2635 | OXA-65; OXA-40; TEM-1 | 32 | 32 | >32 | 0.25 | 16 | >32 | 8 |
| ARC5085 | OXA*; TEM-1 | 32 | 32 | 8 | 1 | 32 | >32 | >32 |
| ARC3657 | OXA-130 | 32 | >32 | 2 | 0.5 | 16 | 0.25 | 8 |
| ARC2636 | OXA-65; OXA-40; TEM-1 | 32 | >32 | >32 | 0.125 | 16 | >32 | 16 |
| ARC2782 | OXA-66; OXA-23; TEM-1; PER-1 | 32 | >32 | 16 | 0.125 | 4 | >32 | >32 |
| ARC3486 | OXA-72; OXA-66; TEM-1 | 32 | >32 | >32 | 0.25 | 8 | >32 | >32 |
| ARC3490 | TEM-1+; PSE-2; OXA-69 | 32 | >32 | 0.5 | 0.5 | 16 | 16 | 8 |
| ARC3495 | OXA-40; OXA-109 | 32 | >32 | >32 | 0.25 | 4 | >32 | >32 |
| ARC3658 | OXA-66; PER-1; TEM-1; OXA-23 | 32 | >32 | 32 | 0.25 | 8 | >32 | >32 |
| ARC5076 | TEM-1; OXA-23; OXA-66 | 32 | >32 | 32 | 0.25 | 8 | 8 | >32 |
| ARC5077 | OXA*; OXA-72 | 32 | >32 | >32 | 0.5 | 16 | >32 | >32 |
| ARC5079 | OXA-72; OXA-65 | 32 | >32 | >32 | 0.125 | 16 | 8 | 8 |
| ARC5080 | OXA-71; OXA-40 | 32 | >32 | >32 | 0.25 | 16 | >32 | 16 |
| ARC5086 | OXA*; TEM-1; OXA-72; OXA-66 | 32 | >32 | >32 | 0.125 | 16 | >32 | >32 |
| ARC5087 | OXA-66; OXA-23 | 32 | >32 | 16 | 0.25 | >32 | >32 | >32 |
| ARC5089 | PER*; TEM-1; OXA-23; OXA-66 | 32 | >32 | 32 | 0.125 | 16 | >32 | 4 |
| ARC3493 | OXA-40; OXA-66 | 64 | >32 | >32 | 32 | 4 | >32 | >32 |
| ARC5074 | GES*; TEM-1; OXA-51 | 64 | >32 | 8 | 0.125 | 4 | 0.125 | 1 |

TABLE 1-continued

Sulbactam shows a wide range of activity against recent clinical strains of *A. baumanii*. Minimal inhibitory concentration (MIC) in μg/mL of each of the following compounds is shown: SUL = sulbactam, UNA = Unasyn, a 2:1 combination of ampicillin and sulbactam, MEM = meropenem, COL = colistin, LEVO = levofloxacin, GENT = gentamycin and TET = tetracycline.

| strain | β-lactamase content | SUL | UNA | MEM | COL | LEVO | GENT | TET |
|---|---|---|---|---|---|---|---|---|
| ARC5082 | OXA-66; OXA-23 | 64 | >32 | >32 | 0.5 | 8 | 0.5 | >32 |
| ARC3882 | OXA-23; NDM-1; OXA-10* | >64 | >32 | >32 | 0.125 | 4 | >32 | 8 |
| | Range | 0.5->64 | 1->32 | <0.03->32 | 0.125->32 | <0.03->32 | 0.06->32 | 0.5->32 |
| | MIC50 | 16 | 32 | 16 | 0.25 | 8 | 64 | 16 |
| | MIC90 | 32 | >32 | 32 | 1 | 32 | >32 | >32 |

§member of the *A. baumannii/calcoaceticus* complex family
*indicates the gene encodes a closely related variant of the indicated β-lactamase family

Example 2: Effect of Ampicillin on MIC for Unasyn® Versus Sulbactam Alone

Figure 2:
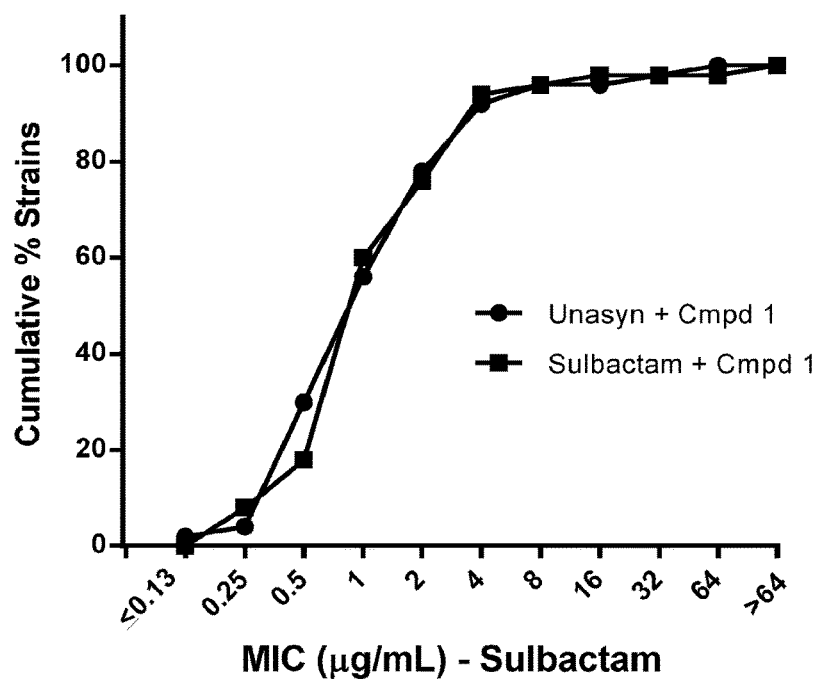
FIG. 2 shows the MIC distribution against A. baumannii isolates for sulbactam+compound 1 and Unasyn®+compound 1, where the amount of sulbactam administered is the same for both combinations tested.

MICs were determined for sulbactam+compound 1 and sulbactam in combination with ampicillin (Unasyn®)+compound 1 according to the method described in Example 1. The dose of Unasyn® was determined so that the total amount of sulbactam administered in both combinations was equivalent. Results show that the activity of Unasyn® is solely dependent on the sulbactam component for effectiveness, and ampicillin has no effect on the efficacy in treating *A. baumannii*. See FIG. 2.

Example 3: Reduction of MIC for Sulbactam+Compound 1 in Recent Clinical Isolates MICs for the combination of sulbactam+compound 1 were determined according to the procedure in Example 1 for a total of 825 recent clinical *A. baumannii* isolates. As shown below, the combination has an $MIC_{90}$ of 4 μg/mL for all isolates, which is the expected breakpoint.

TABLE 2

| | | ≤0.06 | 0.12 | 0.25 | 0.5 | 1 | 2 | 4 | 8 | 16 | 32 | 64 | >64 |
|---|---|---|---|---|---|---|---|---|---|---|---|---|---|
| 2011 | n | 2 | 4 | 20 | 52 | 48 | 45 | 14 | 2 | 3 | 1 | 0 | 0 |
| (n = 191) | % | 1.0 | 2.1 | 10.5 | 27.2 | 23.6 | 23.6 | 7.3 | 1.0 | 1.6 | 0.5 | 0 | 0 |
| | Cum % | 1.0 | 3.1 | 13.6 | 40.8 | 89.5 | 89.5 | 96.8 | 97.8 | 99.4 | 100 | 100 | 100 |
| 2012 | n | 0 | 1 | 5 | 36 | 56 | 67 | 41 | 3 | 0 | 0 | 0 | 0 |
| (n = 209) | % | 0 | 0.5 | 2.4 | 17.2 | 26.8 | 32.1 | 19.6 | 1.4 | 0 | 0 | 0 | 0 |
| | Cum % | 0 | 0.5 | 2.9 | 20.1 | 46.9 | 79.0 | 98.6 | 100 | 100 | 100 | 100 | 100 |
| 2013 | n | 0 | 0 | 9 | 24 | 57 | 63 | 47 | 2 | 3 | 0 | 2 | 0 |
| (n = 207) | % | 0 | 0 | 4.3 | 11.6 | 27.5 | 30.4 | 22.7 | 1.0 | 1.5 | 0 | 1.0 | 0 |
| | Cum % | 0 | 0 | 4.3 | 15.9 | 43.4 | 73.8 | 96.5 | 97.5 | 99.0 | 99.0 | 100 | 100 |
| 2014 | n | 0 | 1 | 16 | 36 | 82 | 54 | 19 | 3 | 1 | 2 | 0 | 4 |
| (n = 218) | % | 0 | 0.5 | 7.3 | 16.5 | 37.6 | 24.8 | 8.7 | 1.4 | 0.5 | 0.9 | 0 | 1.8 |
| | Cum % | 0 | 0.5 | 7.8 | 24.3 | 61.9 | 86.7 | 95.4 | 96.8 | 97.3 | 98.2 | 98.2 | 100 |

Example 4: Sulbactam+Compound 1 Best Combination Partner for *A. baumannii* Infections $MIC_{90}$s were determined for the combination of a number of common antibiotics+compound 1 against a set of 196 contemporary clinical isolates of *A. baumannii*. As shown in Table 3, the sulbactam+compound 1 was the only combination tested which had an $MIC_{90}$ below the CLSI breakpoint. Note that the sulbactam+compound 1 breakpoint was predicted based on the ampicillin:sulbactam (2:1) breakpoint of 2.

TABLE 3

| B-lactam + Cmpd 1 (4 μg/mL) | $MIC_{90}$ (μg/mL) | CLSI (S) Breakpoint |
|---|---|---|
| Sulbactam | 2 | 4 |
| Ceftazidime | 32 | 8* |
| Cefepime | 32 | 8* |
| Imipenem | 16 | 4* |
| Meropenem | 16 | 4* |
| Piperacillin | 32 | 16* |
| Aztreonam | >64 | None* |

*Exceeds breakpoint

Figure 3:
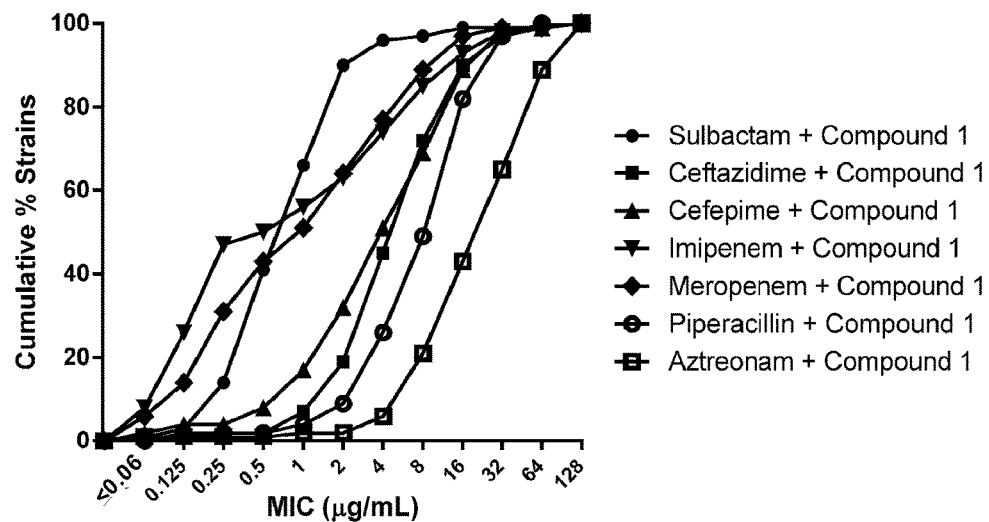
FIG. 3 shows the difference in $MIC_{90}$ for different combinations of β-lactam antibiotic+compound 1 against 196 contemporary *A. baumannii* isolates.

See FIG. 3 for a graphical analysis of the MIC for each tested combination.

Example 5: In Vivo Activity

*Acinetobacter baumannii* Neutropenic Infection Models.

The ability of compound 1 to recover activity versus *A. baumannii* was studied in neutropenic mouse thigh and lung infection models. Briefly, CD-1 mice were rendered neutropenic by injecting cyclophosphamide intraperitoneally 4 days (150 mg/kg of body weight) and 1 day (100 mg/kg) before experimental infection. Mice were infected with a mid-log cultures to achieve a target inoculum of $1 \times 10^6$ CFU for the thigh model or $1 \times 10^7$ CFU for the lung model. Groups of five animals each received subcutaneous injections of either sulbactam alone or sulbactam+compound 1 at a 4:1 ratio eight times daily on a q3h regime starting 2 h after infection. Efficacy was determined 24 h after the start of treatment. Tissue was removed, weighed, homogenized and aliquots plated onto tryptic soy agar plates containing 5% sheep blood/50 μg/mL gentamycin and incubated at 37° C. overnight for CFU determination.

Figure 4:
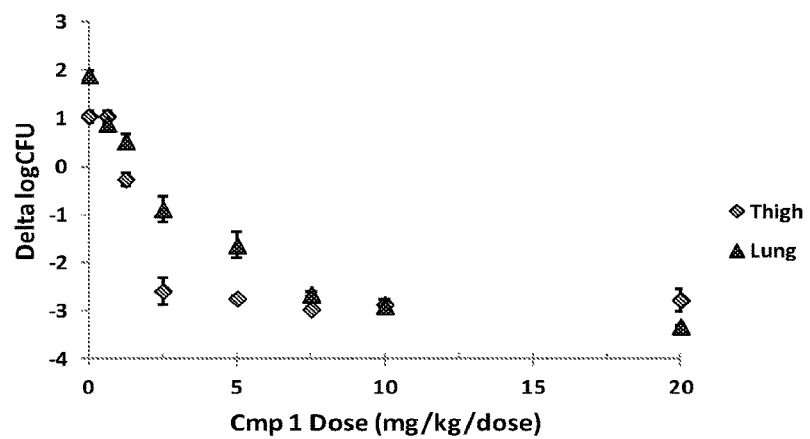
FIG. 4 shows restoration of sulbactam efficacy with compound 1 administered at a constant 4:1 ratio in neutropenic thigh and lung models versus MDR *A. baumannii*.

Compound 1 was shown to recover the activity of isolates of *A. baumannii* which failed to show efficacy with sulbactam alone even when sulbactam plasma exposures were above the in vitro MIC for 24 hours in both model systems. Shown in FIG. 4, efficacy of the combination versus an *A. baumannii* isolate containing AmpC, OXA-66, OXA-72, and TEM-1 shown as mean delta log CFU±standard error of the mean.

Example 6: Efficacy Against *Burkholderia*

Figure 5:
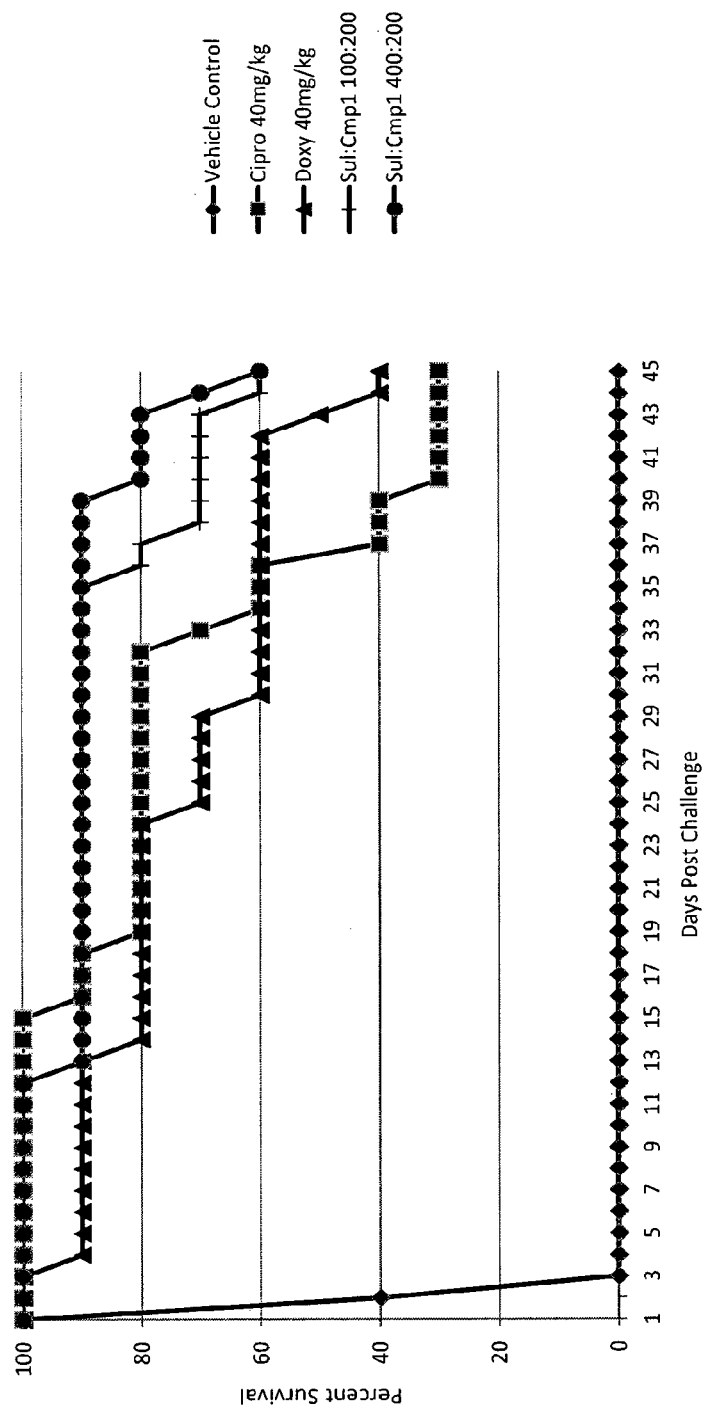
FIG. 5 shows the percent survivorship of mice infected with a lethal dose of *B. pseudomallei* K96243 following 6 consecutive days of treatment with ciprofloxacin, doxycyline and sulbactam:compound 1.

The in vivo activity of sulbactam:compound 1 was assessed against a *B. pseudomallei* clinical isolate (strain K96243, sulbactam:compound 1 MIC=1 mg/L) in an acute murine model of melioidosis. A lethal challenge of K96243 was administered intranasally to Balb/c mice and therapy was initiated 4 hours post challenge followed by six consecutive days of dosing (Table 4). Animals receiving vehicle only generally succumb to the infection within the first 3 days of the study (FIG. 3). Survivors are monitored for 39 days after dosing to evaluate for potential relapse as well as tissue harvesting to confirm eradication of the pathogen. For all studies doxycycline and ciprofloxacin served as positive efficacy controls. In the absence of any PK/PD understanding of sulbactam:compound 1 against this biothreat pathogen, doses where selected based upon initial exposure-effect relatiopnships established in a neutropenic thigh model vs. MDR *Acinetobacter baumannii*. Compound 1 exposure was targeted at time >a threshold concentration of 2.5 mg/L for 40% of the dosing interval and the sulbactam dose was titrated to achieve a concentration range of 40-60% time >the MIC of the combination (1 mg/L). As shown in FIG. 5, both treatment groups with sulbactam:compound 1 were more effective against *B. pseudomallei* K96243 than doxycycline and ciprofloxacin with 60% survivorship achieved vs. 40% and 30% for doxycycline and ciprofloxacin, respectively. See FIG. 5.

TABLE 4

Dosing schedule of ciprofloxacin, doxycyline and sulbactam: compound 1 vs. *B pseudomallei* K96243 in an acute model of melioidosis

| Group | N | Treatment | Dose/shot | Timing | Treatment Route | Infection Route |
|---|---|---|---|---|---|---|
| 1 | 10 | vehicle | N/A | +4 hours, then q4 hours for 6 days | SC | IN |
| 2 | 10 | ciprofloxacin | 40 mg/kg | +4 hours, then BID for 6 days | IP | IN |
| 3 | 10 | doxycycline | 40 mg/kg | +4 hours, then BID for 6 days | IP | IN |
| 4 | 10 | sulbactam: AZ'2514 | 200 mg/kg: 200 mg/kg | +4 hours, then q4 hrs for 6 days | SC | IN |
| 5 | 10 | sulbactam: AZ'2514 | 400 mg/kg: 200 mg/kg | +4 hours, then q4 hrs for 6 days | SC | IN |

SC = subcutaneous
IP = intraperitoneal
IN = intranasal

Figure 6:
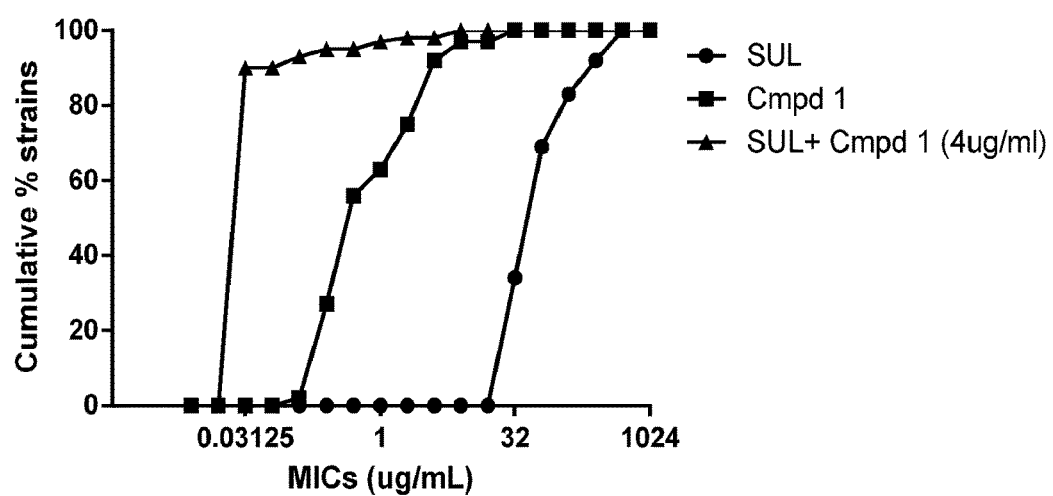
FIG. 6 shows the addition of compound 1 to sulbactam shows significant synergy vs. a panel of 59 recent clinical isolates of Enterobacteriaceae containing known β-lactamase genes.

Example 7: Reduction of MIC for Sulbactam+Compound 1 in Recent Clinical Isolates of Enterobacteraciaea MICs for the combination of sulbactam+compound 1 were determined according to the procedure in Example 1 for a total of 59 recent Enterobacteriaceae clinical isolates. As shown below in Table 5 for each individual strain, and summarized in Table 6, the combination has an $MIC_{90}$ of <0.125 μg/mL for all isolates. See FIG. 6.

TABLE 5

Individual results for Enterobacteriaceae

| Species | strain designation | β-lactamase content | SUL | Cmpd 1 | SUL + Cmpd 1 (4 ug/ml) |
|---|---|---|---|---|---|
| *Escherichia coli* | ARC4 | none (ATCC 25922) CLSI control | 64 | 8 | <0.03 |
| *Escherichia coli* | ARC4416 | CTX-M-14+; TEM-1+ | 32 | 0.5 | <0.03 |
| *Escherichia coli* | ARC4418 | CTX-M-14+; CMY-2+ | 32 | 0.25 | <0.03 |
| *Escherichia coli* | ARC4419 | SHV-12+ | 32 | 0.25 | <0.03 |
| *Escherichia coli* | ARC4421 | CTX-M-55; TEM-1+; CMY-2+ | 64 | 0.25 | 0.25 |
| *Escherichia coli* | ARC4426 | TEM-1+; CMY-2+ | 32 | 0.125 | <0.03 |
| *Escherichia coli* | ARC4429 | TEM-1+; CMY-2+ | 64 | 0.25 | <0.03 |
| *Escherichia coli* | ARC4432 | CTX-M-14+; TEM-1+; CMY-2+ | 128 | 0.25 | <0.03 |
| *Escherichia coli* | ARC4436 | CTX-M-14+; TEM-1+ | 32 | 0.25 | <0.03 |
| *Escherichia coli* | ARC4449 | CMY-2+; TEM-1+ | 64 | 0.5 | <0.03 |
| *Escherichia coli* | ARC4450 | TEM-1+; OXA-1+; CMY-2+ | 64 | 2 | <0.03 |
| *Escherichia coli* | ARC4452 | SHV-12+ | 32 | 0.25 | <0.03 |
| *Escherichia coli* | ARC4455 | SHV-12+ | 32 | 0.25 | <0.03 |

TABLE 5-continued

Individual results for Enterobacteriaceae

| Species | strain designation | β-lactamase content | SUL | Cmpd 1 | SUL + Cmpd 1 (4 ug/ml) |
|---|---|---|---|---|---|
| Escherichia coli | ARC4465 | CMY-2+ | 32 | 0.25 | <0.03 |
| Escherichia coli | ARC4471 | CMY-2+; OXA-1+; TEM-1+ | 128 | 4 | <0.03 |
| Escherichia coli | ARC4472 | CMY-2+; TEM-1+ | 64 | 2 | <0.03 |
| Escherichia coli | ARC4477 | CTX-M-15+; TEM-1+ | 32 | 2 | <0.03 |
| Escherichia coli | ARC4478 | CTX-M-15+; CMY-2+ | 32 | 0.5 | <0.03 |
| Escherichia coli | ARC4479 | CMY-42+; OXA-1+; OXA-9+; TEM-1+ | 64 | 32 | 2 |
| Escherichia coli | ARC4485 | CMY-2+; OXA-1+; CTX-M-15+ | 64 | 0.5 | <0.03 |
| Escherichia coli | ARC4487 | SHV-5+; DHA-1+; TEM-1+; OXA-1+; CMY-2+ | 64 | 4 | <0.03 |
| Klebsiella pneumoniae | ARC4414 | SHV-11 | 32 | 2 | <0.03 |
| Klebsiella pneumoniae | ARC4420 | SHV-11, SHV-12, DHA-1, OXA-1 | 128 | 1 | <0.03 |
| Klebsiella pneumoniae | ARC4427 | SHV-1, OXA-1 | >256 | 0.25 | <0.03 |
| Klebsiella pneumoniae | ARC4434 | SHV-11 | 32 | 2 | <0.03 |
| Klebsiella pneumoniae | ARC4435 | SHV-157 | 32 | 0.25 | <0.03 |
| Klebsiella pneumoniae | ARC4446 | SHV-11 | 32 | 2 | <0.03 |
| Klebsiella pneumoniae | ARC4451 | SHV-11, KPC-3 | >256 | 0.5 | <0.03 |
| Klebsiella pneumoniae | ARC4457 | SHV-11, DHA-1 | 64 | 0.5 | <0.03 |
| Klebsiella pneumoniae | ARC4460 | SHV-11, CTX-M15, OXA-1, NDM-1 | >256 | 4 | <0.03 |
| Klebsiella pneumoniae | ARC4467 | SHV-33, TEM-1, OXA-1, DHA-1 | 64 | 4 | 0.125 |
| Klebsiella pneumoniae | ARC4468 | SHV-1 | 64 | 8 | <0.03 |
| Klebsiella pneumoniae | ARC4476 | SHV-11, KPC-2, OXA-9[W117*] | >256 | 4 | 1 |
| Klebsiella pneumoniae | ARC4480 | SHV-27 | 32 | 0.5 | <0.03 |
| Klebsiella pneumoniae | ARC4482 | SHV-27[A122V], OXA-1 | 32 | 0.5 | <0.03 |
| Klebsiella pneumoniae | ARC4483 | SHV-11 | 32 | 1 | <0.03 |
| Klebsiella pneumoniae | ARC4484 | SHV-168 | 32 | 1 | <0.03 |
| Klebsiella pneumoniae | ARC4486 | SHV-11, DHA-1, OXA-1[E69K] | 128 | 0.5 | <0.03 |
| Klebsiella pneumoniae | ARC4488 | SHV-11, CTX-M15, OXA-1, TEM-1 | 64 | 0.25 | <0.03 |
| Klebsiella pneumoniae | ARC4490 | SHV-11, CTX-M15, KPC-2, OXA-1 | 256 | 0.5 | 0.125 |
| Klebsiella pneumoniae | ARC4495 | SHV-60, LAP-2 | 32 | 4 | <0.03 |
| Enterobacter cloacae | ARC4438 | AmpC+ | 128 | 2 | <0.03 |
| Enterobacter cloacae | ARC4439 | AmpC+; LAP-2+ | 64 | 0.5 | <0.03 |
| Enterobacter cloacae | ARC4444 | AmpC+; MIR-8[I175L] | 64 | 4 | <0.03 |
| Enterobacter cloacae | ARC4458 | AmpC+; ACT-2[V312M] | 64 | 8 | 8 |
| Enterobacter cloacae | ARC4461 | AmpC+; TEM-1 | 64 | 0.25 | <0.03 |
| Enterobacter cloacae | ARC4462 | AmpC+ | 64 | 0.5 | <0.03 |
| Enterobacter cloacae | ARC4473 | SHV-5+; AmpC+; DHA-1+; TEM-1+ | 128 | 0.5 | <0.03 |
| Enterobacter cloacae | ARC4489 | AmpC+ | 128 | 1 | <0.03 |
| Enterobacter cloacae | ARC4492 | AmpC+ | 256 | 0.5 | <0.03 |
| Enterobacter cloacae | ARC4494 | OXA-1+; DHA-1+; AmpC+ | 64 | 0.25 | <0.03 |
| Citrobacter koseri | ARC2001 | ESBL | 64 | 0.5 | <0.03 |
| Citrobacter koseri | ARC2002 | ESBL | 64 | 0.5 | <0.03 |
| Citrobacter freundii | ARC3522 | AmpC, TEM-1, CMY65 | >256 | 0.5 | <0.03 |
| Citrobacter braakii | ARC3660 | CTX-M-15 | 32 | 0.25 | <0.03 |
| Citrobacter freundii | ARC3883 | KPC-2 | 256 | 32 | <0.03 |
| Citrobacter freundii | ARC3884 | KPC-2 | 256 | 4 | <0.03 |
| Citrobacter freundii | ARC3885 | AmpH, TEM-1, SHV-5, CMY-6, CMY-13 | 256 | 4 | <0.03 |

TABLE 6

Summary of results for Enterobacteriaceae

Summary of MICs

| | N | Sulbactam range | Sulbactam $MIC_{50}$ | Sulbactam $MIC_{90}$ | Compound 1 range | Compound 1 $MIC_{50}$ | Compound 1 $MIC_{90}$ | SUL + Cmpd 1 (4 ug/ml) range | SUL + Cmpd 1 $MIC_{50}$ | SUL + Cmpd 1 $MIC_{90}$ |
|---|---|---|---|---|---|---|---|---|---|---|
| *Escherichia coli* | 21 | 32-128 | 64 | 64 | 0.125-32 | 0.5 | 4 | <0.03-2 | <0.03 | <0.03 |
| *Klebsiella pneumoniae* | 20 | 32->256 | 64 | >256 | 0.25-8 | 1 | 4 | <0.03-1 | <0.03 | 0.125 |
| *Enterobacter cloacae* | 10 | 64-256 | 64 | 128 | 0.25-8 | 0.5 | 4 | <0.03-8 | <0.03 | <0.03 |
| *Citrobacter* spp | 7 | 32->256 | 256 | >256 | 0.25-4 | 0.5 | 4 | <0.03-<0.03 | <0.03 | <0.03 |
| Total | 59 | 32->256 | 64 | 256 | 0.125-32 | 0.5 | 4 | <0.03-8 | <0.03 | 0.125 |

Example 8: Synergistic Activity of Sulbactam+Compound 1+Imipenem/Cilastatin or Meropenem in 600 Recent Clinical Isolates of *P. Aeruginosa* and *A. baumannii*

Figure 7:
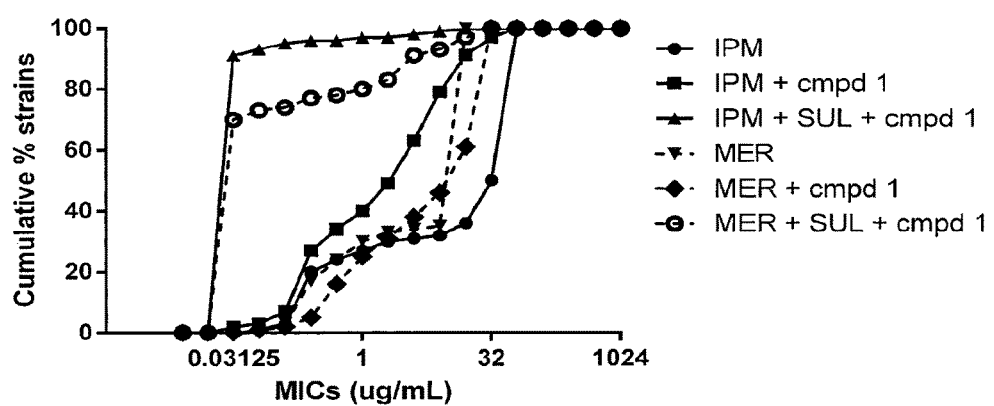
FIG. 7 shows the relative activity of imipenem or meropenem with or without compound 1 at 4 μg/mL or compound 1+sulbactam (each at 4 μg/mL) vs. 600 strains of recent, diverse clinical isolates of *Acinetobacter baumannii*.
Figure 8:
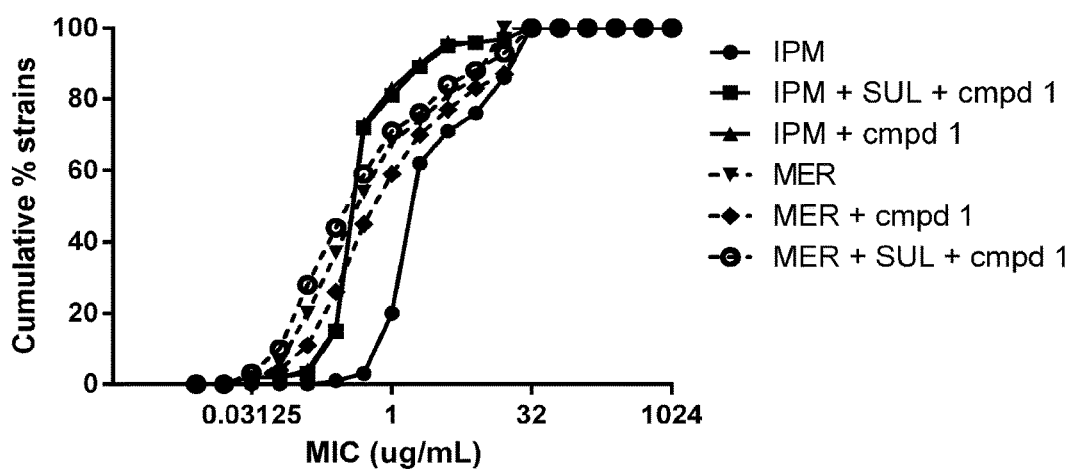
FIG. 8 shows the relative activity of imipenem or meropenem, with or without compound 1 at 4 μg/mL or compound 1+sulbactam (each at 4 μg/mL) vs. 600 strains of recent, diverse clinical isolates of *Pseudomonas aeruginosa*.

600 geographically diverse strains of *Acinetobacter baumannii* or *Pseudomonas aeruginosa* (200 strains of each pathogen from each of 2012, 2013 and 2014) were tested for their susceptibility to imipenem/cilastatin (IPM) or meropenem (MER) alone; imipenem/cilastatin or meropenem in the presence of 4 μg/mL compound 1; or imipenem/cilastatin or meropenem in the presence of a combination of compound 1 and sulbactam each at 4 μg/mL. As shown in Table 7, the inherent antibacterial activity of imipenem or meropenem was much improved by the addition of compound 1 in both *A. baumannii* and *P. aeruginosa* and significantly enhanced by the addition of both sulbactam and compound 1 to *A. baumannii*, whereas the addition of sulbactam to imipenem/cmpd 1 or meropenem/cmpd 1 did not alter the activity of the double combination vs. *P. aeruginosa*. The double combination of imipenem/cilastatin+compound 1 is superior to meropenem+compound 1 vs. both bacterial species and the quad combination of imipenem/cilastatin/sulbactam/compound 1 is measurably superior in activity to that of meropenem/sulbactam/compound 1 in *A. baumannii*. See FIG. 7 and FIG. 8, respectively, for a graphical display of the *A. baumannii* and *P. aeruginosa* results.

Example 9: In Vitro Potentiation of Sulbactam:Compound 1 in Combination with Imipenem Against *A. baumannii* ARC5081

Design. The in vitro activity of sulbactam:compound 1 was assessed against an *A. baumannii* isolate containing OXA-94, OXA-23, and AmpC with and without clinically relevant concentrations of imipenem. Steady state fluctuating free drug concentrations were simulated in an in vitro Hollow-Fiber Infection Model (HFIM) to evaluate bacterial response to varied exposures of sulbactam, compound 1 and imipenem over a period of 24 h. Compounds were administered to the system via a 1 hour infusion and isovolumetrically cleared with a half-life of 2 h. A QID (q6h) regimen was evaluated for all combinations. MICs for all the combinations are summarized in Table 8. A target $C_{max}$ of 10 μg/mL was used for all sulbactam regimens—consistent with achieving a PK/PD endpoint of 50% T>MIC of 4 ug/mL (Table xy). A target $C_{max}$ of 10 μg/mL was also utilized for all imipenem regimens—consistent with achieving a PK/PD endpoint of 50% T>MIC of 4 μg/mL. In all cases, exposure of any one agent was inadequate for achieving efficacy on its own with individual MICs above or near the $C_{max}$ concentrations. Compound 1 was titrated from 1 to 8 μg/mL over the dose ranges of each experiment. Approximately 15 mL of bacteria (inoculum ~5×10⁵ CFU/mL) were grown in cellulosic Hollow Fiber cartridges with dose administration of compound(s) initiated during log phase of growth. Serial samples were collected to determine the actual drug exposure and total bacterial burden. At 24 h, samples were also plated on drug-supplemented plates to determine the resistant bacterial population.

TABLE 7

MIC summary

| | *Acinetobacter baumannii* | | | | *Pseudomonas aeruginosa* | | | |
|---|---|---|---|---|---|---|---|---|
| n = 600 strains | Min | Max | $MIC_{50}$ | $MIC_{90}$ | Min | Max | $MIC_{50}$ | $MIC_{90}$ |
| IPM | 0.06 | >32 | 32 | >32 | 0.06 | >32 | 2 | 32 |
| IPM + cmpd 1 | <0.03 | >32 | 4 | 16 | <0.03 | >32 | 0.5 | 2 |
| IPM + SUL + cmpd 1 | <0.03 | >32 | <0.03 | <0.03 | <0.03 | >32 | 0.5 | 4 |
| MER | 0.0599 | >8 | >8 | >8 | 0.0599 | >8 | 0.5 | >8 |
| MER + cmpd 1 | 0.06 | >32 | 16 | >32 | 0.06 | >32 | 1 | 32 |
| MER + SUL + cmpd 1 | <0.03 | >32 | <0.03 | 4 | <0.03 | >32 | 0.5 | 16 |

TABLE 8

MIC (μg/mL) of imipenem, sulbactam, and compound 1 and selected combinations against an *A. baumannii* isolate containing OXA-94, OXA-23, and AmpC (ARC5081)

| Imipenem | Sulbactam | Compound 1 | Imipenem + Sulbactam @ 4 μg/mL | Imipenem + Compound 1 @ 4 μg/mL | Sulbactam + Compound 1 @ 4 μg/mL | Imipenem + Sulbactam @ 4 μg/ml + Compound 1 @ 4 μg/mL |
|---|---|---|---|---|---|---|
| 16 | 8 | 128 | 4 | 2 | 2 | <0.06 |

TABLE 9

HFIM study design for experimental series evaluating the combination of sulbactam, compound 1, and imipenem against an *A. baumannii* isolate containing OXA-94, OXA-23, and AmpC (ARC5081)

| Isolate/content | Study Design | Sulbactam $C_{max}{}^a$ targeted (μg/mL) | Compound 1 $C_{max}{}^a$ targeted (μg/mL) | Imipenem ($C_{max}{}^a$ targeted (μg/mL) |
|---|---|---|---|---|
| *A. baumannii* OXA-94, OXA-23, and AmpC | 1 Dose Fractionation (QID) | 10 | 0-6 | 0 |
| | 2 Dose Fractionation (QID) | 10 | 0-8 | 10 |

$^a$Peak concentration

Methods.

The Hollow-Fiber cartridge was maintained at 37° C. in an incubator for the duration of the experiment. Bacterial burden (CFU/mL) was serially assessed by sampling (500 μl) from the extra-capillary space of the Hollow-Fiber cartridge at various time points. Serial PK samples (200 μl) were also collected over a 24 h time period to determine simulated drug exposure in all experiments. PK samples were assayed by liquid chromatography-mass spectrometry (LC-MS/MS) to confirm the simulated concentration-time profile. Bacterial samples were diluted (serial 10-fold dilutions) and plate on blood agar plates to enumerate total population. To detect isolates with different magnitudes of reduced susceptibility, agar plates were supplemented with drug. Drug-free blood agar plates were incubated for 24 h and drug-supplemented plates were incubated for up to 72 h (if required) at 37° C. before the colony-forming units were enumerated visually. Drug-supplemented blood agar plates were made using Mueller Hinton Agar supplemented with 5% sheep blood. Serial 10-fold dilutions of the 24 h bacterial samples were plated on a drug-supplemented (4 μg/mL sulbactam, 4 μg/mL compound 1 and 8 μg/mL imipenem) blood agar plates, incubating at 37° C. for 72 h. Any resultant colonies from the drug-supplemented plates were passaged on blood agar plates and were tested for change in MIC against the quad combination. The MIC of each isolate was determined using the broth microdilution method following guidelines of document Clinical and Laboratory Standards Institute (CLSI) guidelines. Clinical Laboratory Standards Institute: Methods for Dilution Antimicrobial Susceptability Tests for Bacteria That Grow Aerobically (10$^{th}$ Ed. (2015)) M07-A10.

Results.

Figure 9:
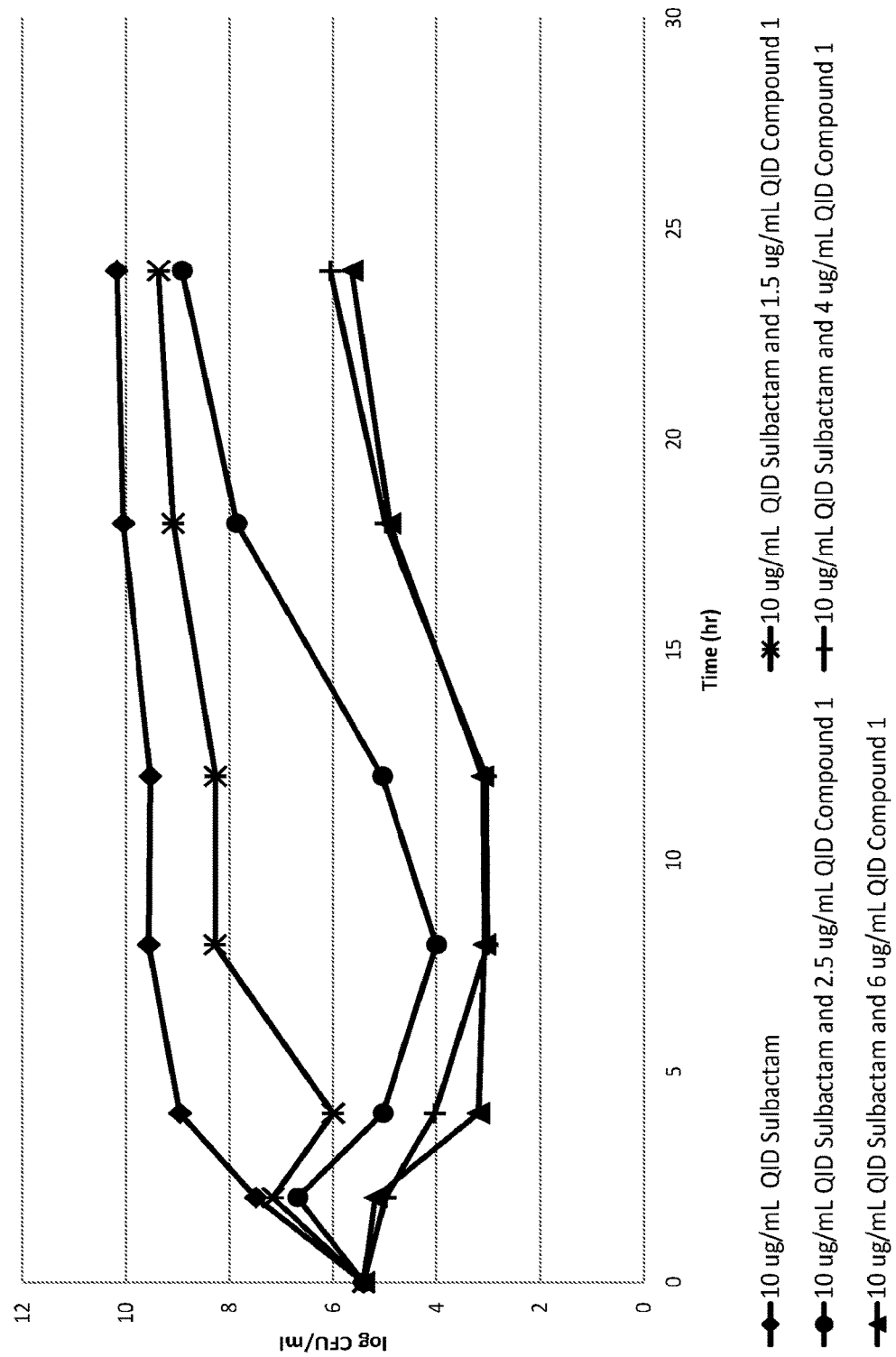
FIG. 9 shows the bacterial burden timecourse of an *A. baumannii* isolate containing OXA-94, OXA-23, and AmpC (ARC5081) following a QID (q6h) regimen of sulbactam with varied doses of compound 1 in in vitro hollow fiber testing.
Figure 10:
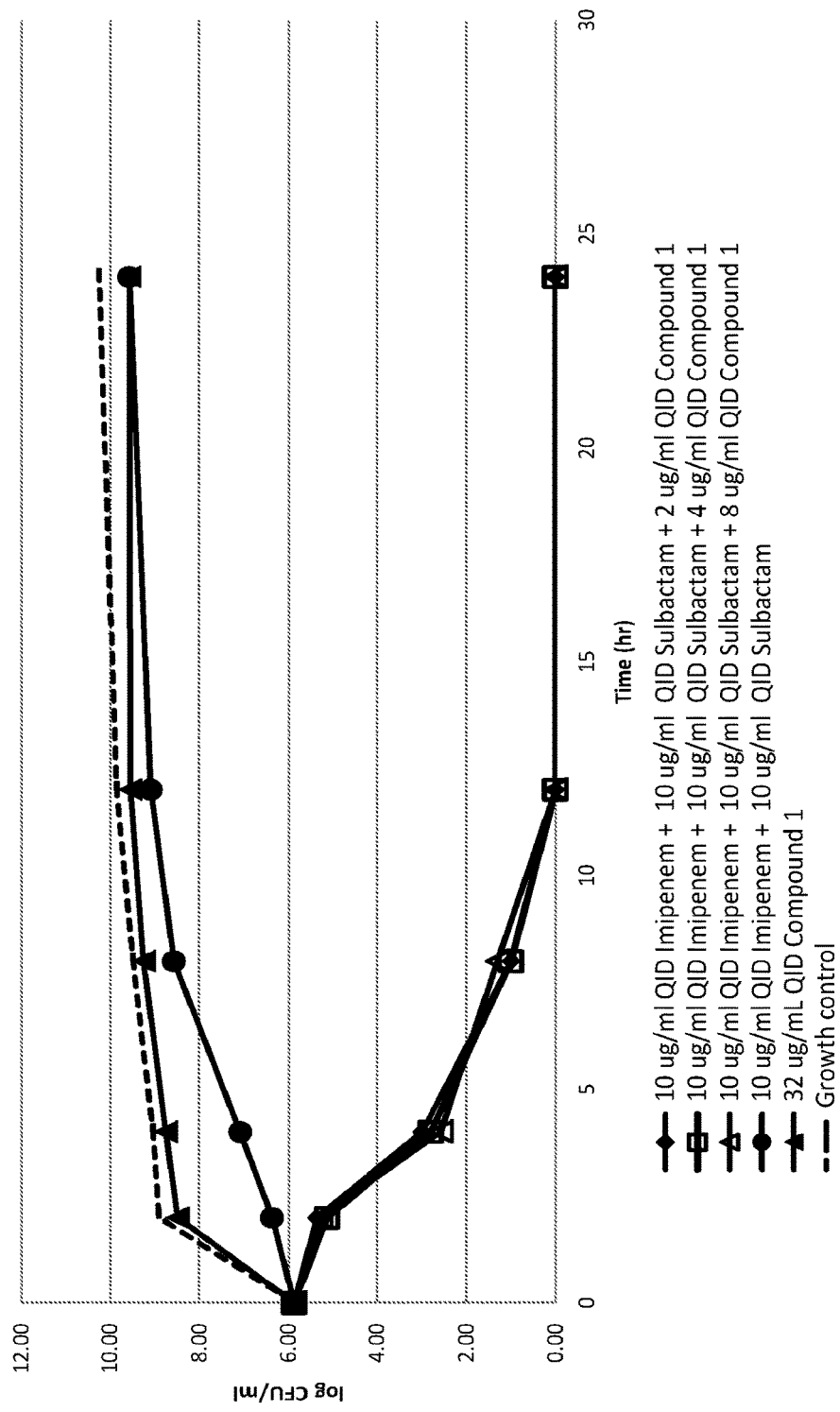
FIG. 10 shows the bacterial burden timecourse of an *A. baumannii* isolate containing OXA-94, OXA-23, and AmpC (ARC5081) following a QID (q6h) regimen of sulbactam and imipenem with varied doses of compound 1 in in vitro hollow fiber testing.

Bacterial burden timecourse following exposure to sulbactam:compound 1 and imipenem:sulbactam:compound 1 are shown in FIG. 9 and FIG. 10, respectively. A regimen of sulbactam with a $C_{max}$ of 10 μg/mL QID resulted in minimal kill and was largely unaffected by the addition of imipenem at an equivalent PK exposure. Addition of compound 1, however, resulted in a rapid and cidal response at $C_{max}$ concentrations as low as 2 μg/mL with no evidence of bacterial regrowth by 24 hours. The observed synergy occurred well below the MIC of compound 1 alone (128 μg/mL) and at concentrations below what is typically required for sufficient β-lactamase inhibition.

Example 10: Sulbactam and Unasyn (2:1 Combination of Ampicillin and Sulbactam) Potentiate Imipenem and Compounds 1 to the Same Extent in *A. baumannii*

20 diverse, recent strains of *A. baumannii* with various β-lactamase content as determined by whole genome sequencing were tested for sensitivity against imipenem, sulbactam, compound 1 or Unasyn (UNA) alone or in combination. Sulbactam and Unasyn had the same effect in each combination. MICs were determined according to the procedure of Example 1, using 20 strains with unique β-lactamase content. Results (Table 10) show that it is only the sulbactam in the Unasyn product which impacts activity of the combination, as they are both equipotent and no advantage is gained by the ampicillin in the Unasyn.

TABLE 10

| Summary of activity | N | Min | Max | $MIC_{50}$ | $MIC_{90}$ |
|---|---|---|---|---|---|
| Cmpd 1 | 20 | 16 | >64 | 64 | >64 |
| IMP | 20 | 0.25 | >64 | 64 | >64 |
| SUL | 20 | 2 | >64 | 16 | 64 |
| UNA | 20 | 1 | >64 | 16 | 64 |
| SUL + Cmpd 1 (4 ug/ml) | 20 | 0.25 | >64 | 1 | 4 |
| UNA + Cmpd 1 (4 ug/ml) | 20 | 0.125 | >64 | 1 | 2 |
| IMP + Cmpd 1 (4 ug/ml) | 20 | 0.125 | >64 | 4 | 32 |
| IMP + UNA (4 ug/ml) | 20 | <0.06 | >64 | 8 | >64 |
| IMP + SUL + Cmpd 1 (each at 4 ug/ml) | 20 | <0.06 | >64 | <0.06 | <0.06 |
| IMP + UNA + Cmpd 1 (each at 4 ug/ml) | 20 | <0.06 | >64 | <0.06 | <0.06 |

Example 11: Synergistic Activity of Sulbactam+Compound 1+Imipenemn in Recent Clinical Isolates of Enterobacteraciaea MICs for the combination of sulbactam+compound 1+imipenem were determined according to the procedure in Example 1 for a total of 59 recent Enterobacteriaceae clinical isolates (the same isolates as shown in Example 7). As summarized below in Table 12, the combination has an $MIC_{90}$ of 0.008 μg/mL for the isolates.

TABLE 12

| | | MIC summary | | | | | | |
|---|---|---|---|---|---|---|---|---|
| | | Imipenem | | Sulbactam | | Cmpd 1 | | IMP + SUL (4 ug/ml) | |
| | N | MIC50 | MIC90 | MIC50 | MIC90 | MIC50 | MIC90 | MIC50 | MIC90 |
| E. coli | 21 | 0.25 | 0.5 | 64 | 64 | 0.5 | 4 | 0.125 | 0.5 |
| K. pneumoniae | 20 | 0.25 | 8 | 64 | >256 | 1 | 4 | 0.125 | >4 |
| Enterobacter cloacae | 10 | 0.5 | 1 | 64 | 128 | 0.5 | 4 | 0.25 | 0.5 |
| Citrobacter spp | 7 | 0.5 | 4 | 256 | >256 | 0.5 | 4 | 0.5 | 4 |
| Total | 59 | 0.5 | 4 | 64 | 256 | 0.5 | 4 | 0.125 | 4 |

| | MIC summary | | | | | |
|---|---|---|---|---|---|---|
| | SUL + Cmpd 1 (4 ug/ml) | | IMP + Cmpd 1 (4 ug/ml) | | IMP + SUL + Cmpd 1 (ea @ 4 ug/ml) | |
| | MIC50 | MIC90 | MIC50 | MIC90 | MIC50 | MIC90 |
| E. coli | <0.03 | <0.03 | <0.004 | <0.004 | <0.004 | 0.008 |
| K. pneumoniae | <0.03 | 0.125 | <0.004 | 0.015 | <0.004 | <0.004 |
| Enterobacter cloacae | <0.03 | <0.03 | <0.004 | <0.004 | <0.004 | <0.004 |
| Citrobacter spp | <0.03 | <0.03 | <0.004 | <0.004 | <0.004 | <0.004 |
| Total | <0.03 | 0.125 | <0.004 | 0.008 | <0.004 | 0.008 |

Example 12: Comparison of Combination of Sulbactam+Compound 1+Imipenemn Against Other β-Lactamase Inhibitor Compounds+Sulbactam+Imipenem MICs were determined for combinations of imipenem+sulbactam+one of the following β-lactamase inhibitors:

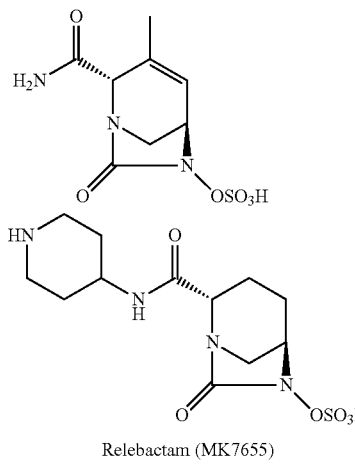

Compound 1

Relebactam (MK7655)

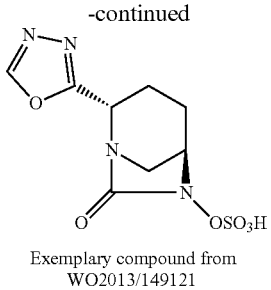

Exemplary compound from WO2013/149121 according to the method described in Example 1. The quad combinations of imipenem/cilastatin, sulbactam and MK7655 or an exemplar compound from WO2013149121A1 were tested against a large panel (n=598) of recent isolates of Acinetobacter baumanni. Results (Table 13) show that the only the combination of compound 1+sulbactam+imipenem/cilastatin was effective at restoring activity against the panel of A. baumannii isolates.

TABLE 13

| MIC summary | | | | |
|---|---|---|---|---|
| combination | # strains | range | MIC50 | MIC90 |
| IMI MIC + SUL & Cmpd 1 (each at 4 ug/mL) | 598 | <0.03 to >32 | 0.03125 | 0.03125 |
| IMI MIC + SUL & MK655 (each at 4 ug/mL) | 598 | <0.03 to >32 | 32 | 32 |
| IMI MIC + SUL & exemplar from WO2013149121A1 (each at 4 ug/mL) | 598 | <0.03 to >32 | 4 | 32 |

The invention claimed is:

1. A combination consisting essentially of the β-lactamase inhibitor:

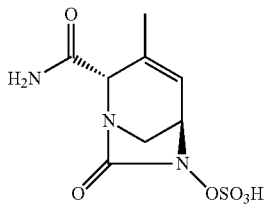

or a pharmaceutically acceptable salt thereof, and sulbactam, or a pharmaceutically acceptable salt thereof.

2. A combination consisting essentially of the β-lactamase inhibitor:

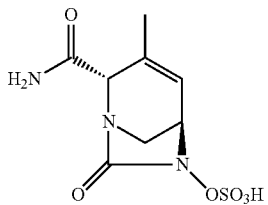

or a pharmaceutically acceptable salt thereof, and sulbactam, or a pharmaceutically acceptable salt thereof, and optionally one or more pharmaceutically acceptable carriers, diluents and/or excipients, and optionally ampicillin or cefoperazone.

3. The combination of claim 1, wherein the β-lactamase inhibitor is in the form of a sodium salt.

4. The combination of claim 1 further comprising ampicillin or cefoperazone.

5. A method of treating bacterial infection in a subject in need thereof, consisting essentially of administering to the subject in need thereof an effective amount of the β-lactamase inhibitor:

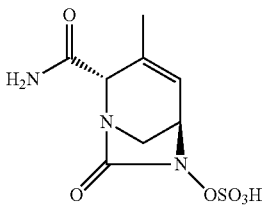

or a pharmaceutically acceptable salt thereof, and an effective amount of sulbactam, or a pharmaceutically acceptable salt thereof.

6. The method of claim 5, wherein the β-lactamase inhibitor is in the form of a sodium salt.

7. The method of claim 5 further comprising ampicillin or cefoperazone.

8. The method of claim 5, wherein the bacterial infection is caused by Enterobacteriaceae.

9. The method of claim 5, wherein the bacterial infection is caused by an *Acinetobacter* spp. pathogen, *Pseudomonas aeruginosa*, or *Burkholderia* spp. pathogen.

* * * * *